(12) United States Patent
Wood et al.

(10) Patent No.: US 10,111,897 B2
(45) Date of Patent: Oct. 30, 2018

(54) COMPOSITIONS AND METHODS FOR TREATING CANCER WITH JAK2 ACTIVITY

(71) Applicant: Duke University, Durham, NC (US)

(72) Inventors: Kris Cameron Wood, Durham, NC (US); Peter Saville Winter, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 0 days.

(21) Appl. No.: 15/027,216

(22) PCT Filed: Oct. 3, 2014

(86) PCT No.: PCT/US2014/059045
§ 371 (c)(1),
(2) Date: Apr. 4, 2016

(87) PCT Pub. No.: WO2015/051252
PCT Pub. Date: Apr. 9, 2015

(65) Prior Publication Data
US 2016/0243150 A1    Aug. 25, 2016

Related U.S. Application Data

(60) Provisional application No. 61/886,130, filed on Oct. 3, 2013, provisional application No. 61/989,105, filed on May 6, 2014.

(51) Int. Cl.
| | |
|---|---|
| *A61K 31/7088* | (2006.01) |
| *A61K 45/06* | (2006.01) |
| *A61K 31/4184* | (2006.01) |
| *A61K 31/428* | (2006.01) |
| *A61K 31/4375* | (2006.01) |
| *A61K 31/519* | (2006.01) |
| *A61K 31/5377* | (2006.01) |
| *A61K 31/4745* | (2006.01) |
| *A61K 31/506* | (2006.01) |
| *A61K 31/635* | (2006.01) |
| *A61K 31/4178* | (2006.01) |
| *A61K 31/366* | (2006.01) |
| *A61K 31/404* | (2006.01) |
| *A61K 31/553* | (2006.01) |
| *A61K 31/675* | (2006.01) |
| *G01N 33/68* | (2006.01) |

(52) U.S. Cl.
CPC ........ *A61K 31/7088* (2013.01); *A61K 31/366* (2013.01); *A61K 31/404* (2013.01); *A61K 31/4178* (2013.01); *A61K 31/4184* (2013.01); *A61K 31/428* (2013.01); *A61K 31/4375* (2013.01); *A61K 31/4745* (2013.01); *A61K 31/506* (2013.01); *A61K 31/519* (2013.01); *A61K 31/5377* (2013.01); *A61K 31/553* (2013.01); *A61K 31/635* (2013.01); *A61K 31/675* (2013.01); *A61K 45/06* (2013.01); *G01N 33/6893* (2013.01); *G01N 2333/9121* (2013.01); *G01N 2800/52* (2013.01); *G01N 2800/7028* (2013.01)

(58) Field of Classification Search
CPC ..................................................... A61K 48/00
See application file for complete search history.

(56) References Cited

U.S. PATENT DOCUMENTS

| | | | |
|---|---|---|---|
| 2008/0131526 A1 | 6/2008 | Sebti et al. | |
| 2010/0310648 A1 | 12/2010 | Packhaeuser et al. | |
| 2010/0311751 A1 | 12/2010 | Schmitt et al. | |
| 2013/0035253 A1 | 2/2013 | Rosen et al. | |

FOREIGN PATENT DOCUMENTS

| | | |
|---|---|---|
| EP | 1622616 | 6/2011 |
| WO | 2013037943 | 3/2013 |
| WO | 2013059320 | 4/2013 |

OTHER PUBLICATIONS

Verstovsek eta I. (N Engl J Med 2010; 363-1117-1127).*
Bhagwat et al. Sensitivity and resistance of JAK2 inhibitors to myeloproliferative neoplasms, International Journal of Hematology, May 14, 2013 (May 14, 2013), vol. 97, pp. 695-702. entire document.
Will et al. "Apoptosis induced by JAK2 inhibition is mediated by Bim and enhanced by the BH3 mimeticABT-737 in JAK2 mutant human erythroid cells," Blood, Apr. 8, 2010 (Apr. 8, 2010), vol. 115, No. 14, pp. 2901-2910. entire document.
Suryani et al. "Dual Inhibition of JAK/STAT and Mark Pathways Results in Synergistic Cell Killing of JAK-Mutated Pediatric Acute Lymphoblastic Leukemia," Blood, Dec. 8, 2012 (Dec. 8, 2012), vol. 120, Abstract 3562. entire document.
Lazo et al. "Pharmacologic Profiling of Phosphoinositide 3-Kinase Inhibitors as Mitigators of Ionizing Radiation-Induced Cell Death," The Journal of Pharmacology and Experimental Therapeutics, Sep. 25, 2013 (Sep. 25, 2013), vol. 347, pp. 669-680. entire document.
The International Search Report and Written Opinion dated Jan. 29, 2015 for International Application PCT/2014/059045.

* cited by examiner

*Primary Examiner* — Kimberly Chong
(74) *Attorney, Agent, or Firm* — Quarles & Brady LLP

(57) ABSTRACT

Methods and compositions for diagnosing and treating JAK2 inhibitor resistant cancers are disclosed. In the disclosed methods, AKT and/or PI3K inhibitors, ERK/MEK inhibitors, BCL-XL protein inhibitors, or combinations thereof are administered to a subject to reverse JAK2 inhibitor resistance. Accordingly, compositions containing such inhibitors may be used along with JAK2 inhibitors to successfully treat JAK2 inhibitor resistant cancers.

11 Claims, 13 Drawing Sheets
Specification includes a Sequence Listing.

SEQUENCE LISTING

```
<160> NUMBER OF SEQ ID NOS: 8

<210> SEQ ID NO 1
<211> LENGTH: 48
<212> TYPE: DNA
<213> ORGANISM: Artificial Sequence
<220> FEATURE:
<223> OTHER INFORMATION: shBAD_54 construct

<400> SEQUENCE: 1
gacgagtttg tggactcctt tctcgagaaa ggagtccaca aactcgtc          48

<210> SEQ ID NO 2
<211> LENGTH: 48
<212> TYPE: DNA
<213> ORGANISM: Artificial Sequence
<220> FEATURE:
<223> OTHER INFORMATION: shBAD_56 construct

<400> SEQUENCE: 2
ccagtcctgg tgggatcgga actcgagttc cgatcccacc aggactgg          48

<210> SEQ ID NO 3
<211> LENGTH: 48
<212> TYPE: DNA
<213> ORGANISM: Artificial Sequence
<220> FEATURE:
<223> OTHER INFORMATION: shJAK2 (1) construct

<400> SEQUENCE: 3
gctttgtctt tcgtgtcatt actcgagtaa tgacacgaaa gacaaagc          48

<210> SEQ ID NO 4
<211> LENGTH: 48
<212> TYPE: DNA
<213> ORGANISM: Artificial Sequence
<220> FEATURE:
<223> OTHER INFORMATION: shJAK2 (2) construct

<400> SEQUENCE: 4
gcagaattag caaaccttat actcgagtat aaggtttgct aattctgc          48

<210> SEQ ID NO 5
<211> LENGTH: 20
<212> TYPE: DNA
<213> ORGANISM: Artificial Sequence
<220> FEATURE:
<223> OTHER INFORMATION: Human Pim1 forward primer

<400> SEQUENCE: 5
ttatcgacct caatcgcggc                                         20

<210> SEQ ID NO 6
<211> LENGTH: 20
<212> TYPE: DNA
<213> ORGANISM: Artificial Sequence
<220> FEATURE:
<223> OTHER INFORMATION: Human Pim1 reverse primer

<400> SEQUENCE: 6
ggtagcgatg gtagcggatc                                         20

<210> SEQ ID NO 7
<211> LENGTH: 20
<212> TYPE: DNA
<213> ORGANISM: Artificial Sequence
```

-continued

```
<220> FEATURE:
<223> OTHER INFORMATION: Human GAPDH forward primer

<400> SEQUENCE: 7
cccactcctc cacctttgac                                               20

<210> SEQ ID NO 8
<211> LENGTH: 20
<212> TYPE: DNA
<213> ORGANISM: Artificial Sequence
<220> FEATURE:
<223> OTHER INFORMATION: Human GAPDH reverse primer

<400> SEQUENCE: 8
accctgttgc tgtagccaaa                                               20
```

COMPOSITIONS AND METHODS FOR TREATING CANCER WITH JAK2 ACTIVITY

CROSS-REFERENCE TO RELATED APPLICATIONS

This application represents the US National Stage of International Application PCT/US14/59045, filed Oct. 3, 2014, which claims benefit of and incorporates herein by reference in its entirety, U.S. Provisional Patent Application 61/989,105, filed May 6, 2014 and U.S. Provisional Patent Application 61/886,130, filed Oct. 3, 2013.

STATEMENT REGARDING FEDERALLY FUNDED RESEARCH AND DEVELOPMENT

N/A

BACKGROUND OF THE DISCLOSURE

Myeloproliferative neoplasms (MPN) are a class of hematologic makignancies arising from haematopoietic progenitors, and include diseases such as chronic myeloid leukemia (CML), polycythaemia vera (PV), essential thrombocythaemia (ET) and primary myelofibrosis (PMF). In 2005, a recurrent somatic point mutation in the pseudokinase domain of the Janus kinase 2 (JAK2) gene was discovered to be present in a large proportion of patients suffering from these diseases (see, e.g., Levine, R. et al. 2005, *Cancer Cell* 7:387; James, C. et al. 2005, *Nature* 434:1144). Specifically, in patients with PV, ET, and PMF the activating JAK2$^{V617F}$ mutation occurs with a frequency of between 81-99%, 41-72% and 39-57% respectively (see, e.g., Levine, R. L. et al. 2007, *Nat. Rev. Cancer* 7:673). Additionally, over-activation of JAK/STAT signaling has been described in a subset of patients that do not harbor JAK mutations (see, e.g., Quintas-Cardanam A. et al. 2013, Clinical Cancer Res. Doi:10.1158/1078-0432.CCR-12-0284). Taken together, evidence to date supports the targeting of the JAK/STAT pathway, specifically JAK2, in patients with various MPNs.

Recently, clinical trials have been carried out to evaluate the efficacy of the second generation JAK1 and JAK2 inhibitor ICNB018424 in patients suffering from MPNs. The conclusions of these trials show that, while transiently effective at reducing spleen size and alleviating some symptoms (in about 50% of patients), INCB018424-resistance is a real problem facing the drug moving forward in the clinic. A significant fraction of patients will experience suboptimal responses, and a few, if any, will see a substantial reduction in JAK2$^{V617F}$ allele burden (see, e.g., Verstovsek, S. et al. 2012, *N. Eng. J. Med.* 366:799; Tefferi, A. et al., 2012, *N. Eng. J. Med.* 366:844; and Tefferi, A. et al., 2012, *Blood* 119:2721). Treatment failures seen in the clinic could be due to: (1) second site mutations in the kinase domain (see, e.g., Deshpande, A. et al. 2011, *Leukemia* 26:708); (2) heterodimerization of activated JAK2 and JAK1 or TYK2, leading to reactivation of signaling to downstream STAT proteins (see, e.g., Koppikar, P. et al. 2012, *Nature* 489:155); (3) previously uncharacterized downstream or parallel pathway activation (see, e.g., Poulikakos, P. I. et al. 2011, *Cancer Cell* 19:11); or (4) some combination of these three.

In light of the development of JAK2 inhibitor resistance in the treatment of some cancers, there is a need to understand and develop effective therapies for the treatment of cancers having developed resistance to JAK2 inhibitors.

SUMMARY OF THE DISCLOSURE

The present disclosure relates to our surprising discovery that in certain cancers conventionally treated with JAK inhibitors, combined inhibition of JAK2 and Ras effector pathways, or the direct, selective inhibition of BCL-X$_L$ protein, yields more robust and durable responses than JAK inhibitor monotherapy.

Accordingly, in a first aspect, the disclosure encompasses a method of treating cancer in a subject in need thereof. The method includes the step of administering to the subject an effective amount of (a) an AKT and/or PI3K inhibitor; (b) an ERK/MEK inhibitor; (c) a BCL-X$_L$ protein inhibitor; or (d) any combination thereof; whereby the cancer is successfully treated.

In some embodiments, the AKT and/or PI3K inhibitor is AZD5363, VQD-002, Perifosine, Wortmannin, demthozyviridin, LY294002, CAL101, PX-866, IPI-145, BAY 80-6946, BEX235, RP6503, TGR 1202, SF1126, INKL 117, GDC-0941, BKMI20, XL147, XL765, Palomid 529, GSK1059615, ZSTK474, PWT33597, 1C87114, TG100-115, CAL263, RP6530, PI-103, GNE-477, CUDC-907, AEZS-136, or combinations thereof.

In some embodiments, the ERK/MEK inhibitor is Trametinib, Selumetinib, MEK162, PD-325901, XL518, CI-1040, PD035901, or combinations thereof.

In some embodiments, the BCL-X$_L$ protein inhibitor is ABT-737, ABT-263, ABT-199, Genasense, obatoclax, or combinations thereof.

In some embodiments, the cancer is a myelproliferative neoplasm. Non-limiting examples of such neoplasms include chronic myeloid leukemia (CML), acute myeloid leukemia (AML), polycythaemia vera (PCV), essential thrombocythaemia (ET), primary myelofibrosis (PMF), chronic eosinophilic leukemia (CEL), chronic myelomonocytic leukemia (CMML), systemic mastocytosis (SM), idiopathic myelofibrosis (IMF), and myeloma.

In some embodiments, the cancer is resistant to JAK2 inhibitor-based therapy. In some embodiments, the subject has an activated AKT pathway. In some embodiments, the cancer has a JAK2$^{V617F}$ mutation.

In some embodiments, the method further includes the step of administering a JAK2 inhibitor to the subject. Exemplary JAK2 inhibitors include without limitation INCB018424/Ruxolitinib, Tofacitinub, Baricitnib, CYT387, Lestaurtinib, Pacritinib, TG101348, and combinations thereof. In some embodiments, the AKT and/or PI3K inhibitor, the ERK/MEK inhibitor, the BCL-X$_L$ protein inhibitor, or any combination thereof is administered before or concurrently with the JAK2 inhibitor.

In some embodiments, both the AKT and/or PI3K inhibitor and the ERK/MEK inhibitor are administered.

In some embodiments, the BCL-X$_L$ protein inhibitor is administered and no JAK2 inhibitor is administered. In some such embodiments, no AKT and/or PI3K inhibitor and no ERK/MEK inhibitor is administered.

In a second aspect, the disclosure encompasses an AKT and/or PI3K inhibitor for use in treating cancer. Exemplary AKT and/or PI3K inhibitors include without limitation AZD5363, VQD-002, Perifosine, Wortmannin, demthozyviridin, LY294002, CAL101, PX-866, IPI-145, BAY 80-6946, BEX235, RP6503, TGR 1202, SF1126, INK1117, GDC-0941, BKMI20, XL147, XL765, Palomid 529, GSK1059615, ZSTK474, PWT33597, 1C87114, TG100-115, CAL263, RP6530, PI-103, GNE-477, CUDC-907, AEZS-136, and combinations thereof.

In a third aspect, the disclosure encompasses an ERK/MEK inhibitor for use in treating cancer. Exemplary ERK/MEK inhibitor s include without limitation Trametinib, Selumetinib, MEK162, PD-325901, XL518, CI-1040, PD035901, and combinations thereof.

In a fourth aspect, the disclosure encompasses a BCL-$X_L$ protein inhibitor for use in treating cancer. Exemplary BCL-$X_L$ protein inhibitors include without limitation ABT-737, ABT-263, ABT-199, Genasense, obatoclax, and combinations thereof.

In some embodiments of the second, third, and fourth aspects, the cancer is a myelproliferative neoplasm. Exemplary myeloproliferative neoplasms include without limitation chronic myeloid leukemia (CML), acute myeloid leukemia (AML), polycythaemia vera (PCV), essential thrombocythaemia (ET), primary myelofibrosis (PMF), chronic eosinophilic leukemia (CEL), chronic myelomonocytic leukemia (CMML), systemic mastocytosis (SM), idiopathic myelofibrosis (IMF), and myeloma. In some embodiments of the second, third, and fourth aspects, the cancer is resistant to JAK2 inhibitor-based therapy. In some embodiments of the second, third, and fourth aspects, the cancer has an activated AKT pathway. In some embodiments of the second, third, and fourth aspects, the cancer includes a $JAK2^{V617F}$ mutation.

In some embodiments of the second, third, and fourth aspects, the use of the inhibitor includes co-administering a JAK2 inhibitor. Exemplary JAK2 inhibitors include without limitation INCB018424/Ruxolitinib, Tofacitinub, Baricitnib, CYT387, Lestaurtinib, Pacritinib, TG101348, and combinations thereof.

In some embodiments of the fourth aspect, the use of the BCL-$X_L$ protein inhibitor does not include co-administering a JAK2 inhibitor. In some embodiments, the use of the BCL-$X_L$ protein inhibitor does not include co-administering an AKT and/or PI3K inhibitor or an ERK/MEK inhibitor.

In a fifth aspect, the disclosure encompasses a composition including both an AKT and/or PI3K inhibitor and an ERK/MEK inhibitor for use in treating cancer. Exemplary AKT and/or PI3K include without limitation AZD5363, VQD-002, Perifosine, Wortmannin, demthozyviridin, LY294002, CAL101, PX-866, IPI-145, BAY 80-6946, BEX235, RP6503, TGR 1202, SF1126, INK1117, GDC-0941, BKMI20, XL147, XL765, Palomid 529, GSK1059615, ZSTK474, PWT33597, 1C87114, TG100-115, CAL263, RP6530, PI-103, GNE-477, CUDC-907, AEZS-136, and combinations thereof. Exemplary ERK/MEK inhibitors include without limitation Trametinib, Selumetinib, MEK162, PD-325901, XL518, CI-1040, PD035901, and combinations thereof.

In some embodiments, the cancer is a myelproliferative neoplasm. Exemplary myeloproliferative neoplasms include without limitation chronic myeloid leukemia (CML), acute myeloid leukemia (AML), polycythaemia vera (PCV), essential thrombocythaemia (ET), primary myelofibrosis (PMF), chronic eosinophilic leukemia (CEL), chronic myelomonocytic leukemia (CMML), systemic mastocytosis (SM), idiopathic myelofibrosis (IMF), and myeloma.

In a sixth aspect, the disclosure encompasses an AKT and/or PI3K inhibitor for use in manufacturing a medicament for treating cancer. Exemplary AKT and/or PI3K inhibitors include without limitation AZD5363, VQD-002, Perifosine, Wortmannin, demthozyviridin, LY294002, CAL101, PX-866, IPI-145, BAY 80-6946, BEX235, RP6503, TGR 1202, SF1126, INK1117, GDC-0941, BKMI20, XL147, XL765, Palomid 529, GSK1059615, ZSTK474, PWT33597, 1C87114, TG100-115, CAL263, RP6530, PI-103, GNE-477, CUDC-907, AEZS-136, and combinations thereof.

In a seventh aspect, the disclosure encompasses an ERK/MEK inhibitor for use in manufacturing a medicament for treating cancer. Exemplary ERK/MEK inhibitors include without limitation Trametinib, Selumetinib, MEK162, PD-325901, XL518, CI-1040, PD035901, and combinations thereof.

In an eighth aspect, the disclosure encompasses a BCL-$X_L$ protein inhibitor for use in manufacturing a medicament for treating cancer. Exemplary BCL-$X_L$ protein inhibitors include without limitation ABT-737, ABT-263, ABT-199, Genasense, obatoclax, and combinations thereof.

In some embodiments, the cancer is a myelproliferative neoplasm. Exemplary myeloproliferative neoplasms include without limitation chronic myeloid leukemia (CML), acute myeloid leukemia (AML), polycythaemia vera (PCV), essential thrombocythaemia (ET), primary myelofibrosis (PMF), chronic eosinophilic leukemia (CEL), chronic myelomonocytic leukemia (CMML), systemic mastocytosis (SM), idiopathic myelofibrosis (IMF), and myeloma.

In some embodiments, the cancer is resistant to JAK2 inhibitor-based therapy. In some embodiments, the cancer has an activated AKT pathway. In some embodiments, the cancer includes a $JAK2^{V617F}$ mutation.

In some embodiments of the sixth, seventh, and eighth aspects, the medicament is to be co-administered with a JAK2 inhibitor. Exemplary JAK2 inhibitors include without limitation INCB018424/Ruxolitinib, Tofacitinub, Baricitnib, CYT387, Lestaurtinib, Pacritinib, TG101348, and combinations thereof.

In some embodiments of the eighth aspect, the medicament is not to be co-administered with a JAK2 inhibitor. In some embodiments of the eighth aspect, the medicament is not to be co-administered with an AKT and/or PI3K inhibitor or an ERK/MEK inhibitor.

In a ninth aspect, the disclosure encompasses a composition comprising both an AKT and/or PI3K inhibitor and an ERK/MEK inhibitor for use in manufacturing a medicament for treating cancer. Exemplary AKT and/or PI3K inhibitors include without limitation AZD5363, VQD-002, Perifosine, Wortmannin, demthozyviridin, LY294002, CAL101, PX-866, IPI-145, BAY 80-6946, BEX235, RP6503, TGR 1202, SF1126, INK1117, GDC-0941, BKMI20, XL147, XL765, Palomid 529, GSK1059615, ZSTK474, PWT33597, 1C87114, TG100-115, CAL263, RP6530, PI-103, GNE-477, CUDC-907, AEZS-136, and combinations thereof. Exemplary ERK/MEK inhibitors include without limitation Trametinib, Selumetinib, MEK162, PD-325901, XL518, CI-1040, PD035901, and combinations thereof.

In some embodiments, the cancer is a myelproliferative neoplasm. Exemplary myeloproliferative neoplasms include without limitation chronic myeloid leukemia (CML), acute myeloid leukemia (AML), polycythaemia vera (PCV), essential thrombocythaemia (ET), primary myelofibrosis (PMF), chronic eosinophilic leukemia (CEL), chronic myelomonocytic leukemia (CMML), systemic mastocytosis (SM), idiopathic myelofibrosis (IMF), and myeloma.

In a tenth aspect, the disclosure encompasses a method of sensitizing a subject to a JAK2 inhibitor wherein the subject has developed resistance to a JAK2 inhibitor-based therapy and has an activated AKT pathway. The method includes the step of administering to the subject a therapeutically effective amount of an AKT and/or PI3K inhibitor in combination with the JAK2 inhibitor, whereby the subject is sensitized to the JAK2 inhibitor.

In some embodiments, the AKT and/or PI3K inhibitor is administered before or concurrently with the JAK2 inhibitor.

Exemplary AKT and/or PI3K inhibitors include without limitation AZD5363, VQD-002, Perifosine, Wortmannin, demthozyviridin, LY294002, CAL101, PX-866, IPI-145, BAY 80-6946, BEX235, RP6503, TGR 1202, SF1126, INK1117, GDC-0941, BKM120, XL147, XL765, Palomid 529, GSK1059615, ZSTK474, PWT33597, 1C87114, TG100-115, CAL263, RP6530, PI-103, GNE-477, CUDC-907, AEZS-136, and combinations thereof.

In an eleventh aspect, the disclosure encompasses a method of sensitizing a subject to a JAK2 inhibitor wherein the subject has developed resistance to a JAK2 inhibitor-based therapy and has an activated ERK pathway. The method includes the step of administering to the subject a therapeutically effective amount of an ERK/MEK inhibitor in combination with the JAK2 inhibitor, whereby the subject is sensitized to the JAK2 inhibitor.

In some embodiments, the ERK/MEK inhibitor is administered before or concurrently with the JAK2 inhibitor Exemplary ERK/MEK inhibitors include without limitation Trametinib, Selumetinib, MEK162, PD-325901, XL518, CI-1040, PD035901, and combinations thereof.

In a twelfth aspect, the disclosure encompasses a method of sensitizing a subject to a JAK2 inhibitor wherein the subject has developed resistant to a JAK2 inhibitor-based therapy and has an activated AKT and ERK pathway. The method includes the step of administering to the subject a therapeutically effective amount of an AKT and/or PI3K inhibitor and an ERK/MEK inhibitor in combination with the JAK2 inhibitor, whereby the subject is sensitized to the JAK2 inhibitor.

In some embodiments, the AKT and/or PI3K inhibitor and the ERK/MEK inhibitor are administered before or concurrently with the JAK2 inhibitor.

Exemplary AKT and/or PI3K inhibitors include without limitation AZD5363, VQD-002, Perifosine, Wortmannin, demthozyviridin, LY294002, CAL101, PX-866, IPI-145, BAY 80-6946, BEX235, RP6503, TGR 1202, SF1126, INK1117, GDC-0941, BKMI20, XL147, XL765, Palomid 529, GSK1059615, ZSTK474, PWT33597, 1C87114, TG100-115, CAL263, RP6530, PI-103, GNE-477, CUDC-907, AEZS-136, and combinations thereof. Exemplary ERK/MEK inhibitors include without limitation include Trametinib, Selumetinib, MEK162, PD-325901, XL518, CI-1040, PD035901, and combinations thereof.

In a thirteenth aspect, the disclosure encompasses a method of reversing resistance to JAK2 inhibitor therapy in a subject wherein the subject has an activated AKT pathway. The method includes the step of administering to the subject a therapeutically effective amount of an AKT and/or PI3K inhibitor in combination with the JAK2 inhibitor, whereby the subject's resistance to JAK2 inhibitor therapy is reversed.

In some embodiments, the AKT and/or PI3K inhibitor is administered before or concurrently with the JAK2 inhibitor.

Exemplary AKT and/or PI3K inhibitors include without limitation AZD5363, VQD-002, Perifosine, Wortmannin, demthozyviridin, LY294002, CAL01, PX-866, IPI-145, BAY 80-6946, BEX235, RP6503, TGR 1202, SF1126, INK1117, GDC-0941, BKMI20, XL147, XL765, Palomid 529, GSK1059615, ZSTK474, PWT33597, 1C87114, TG100-115, CAL263, RP6530, PI-103, GNE-477, CUDC-907, AEZS-136, and combinations thereof.

In a fourteenth aspect, the disclosure encompasses a method of reversing resistance to JAK2 inhibitor therapy in a subject wherein the subject has an activated ERK/MEK pathway. The method includes the step of administering to the subject a therapeutically effective amount of an ERK/MEK inhibitor in combination with the JAK2 inhibitor, whereby the subject's resistance to JAK2 inhibitor therapy is reversed.

In some embodiments, the ERK/MEK inhibitor is administered before or concurrently with the JAK2 inhibitor.

Exemplary ERK/MEK inhibitors include without limitation Trametinib, Selumetinib, MEK162, PD-325901, XL518, CI-1040, PD035901, and combinations thereof.

In a fifteenth aspect, the disclosure encompasses a method of reversing resistance to JAK2 inhibitor therapy in a subject wherein the subject has an activated AKT and ERK/MEK pathway. The method includes the step of administering to the subject a therapeutically effective amount of an AKT and/or PI3K inhibitor and an ERK/MEK inhibitor in combination with the JAK2 inhibitor, whereby the subject's resistance to JAK2 inhibitor therapy is reversed.

In some embodiments, the AKT and/or PI3K inhibitor and the ERK/MEK inhibitor are administered before or concurrently with the JAK2 inhibitor.

Exemplary AKT and/or PI3K inhibitors include without limitation AZD5363, VQD-002, Perifosine, Wortmannin, demthozyviridin, LY294002, CAL101, PX-866, IPI-145, BAY 80-6946, BEX235, RP6503, TGR 1202, SF1126, INK1117, GDC-0941, BKMI20, XL147, XL765, Palomid 529, GSK1059615, ZSTK474, PWT33597, 1C87114, TG100-115, CAL263, RP6530, PI-103, GNE-477, CUDC-907, AEZS-136, and combinations thereof. Exemplary ERK/MEK inhibitors include without limitation Trametinib, Selumetinib, MEK162, PD-325901, XL518, CI-1040, PD035901, and combinations thereof.

In a sixteenth aspect, the disclosure encompasses a method of sensitizing a subject to a JAK2 inhibitor wherein the subject has developed resistance to a JAK2 inhibitor-based therapy and has at least one phosphorylated BAD- and/or activated BCL-$X_L$ protein. The method includes the step of administering to the subject a therapeutically effective amount of a BCL-$X_L$ protein inhibitor in combination with the JAK2 inhibitor, whereby the subject is sensitized to the JAK2 inhibitor.

In a seventeenth aspect, the disclosure encompasses a method of reversing resistance to JAK2 inhibitor therapy in a subject wherein the subject has at least one phosphorylated BAD- and/or activated BCL-$X_L$ protein. The method includes the step of administering to the subject a therapeutically effective amount of a BCL-$X_L$ protein inhibitor, whereby the subject's resistance to the JAK2 inhibitor therapy is reversed.

In a eighteenth aspect, the disclosure encompasses a method of treating a subject having resistance to JAK2 inhibitor therapy and at least one phosphorylated BAD- and/or activated BCL-$X_L$ protein. The method includes the step of administering to the subject a therapeutically effective amount of a BCL-$X_L$ protein inhibitor.

In some embodiments, the BCL-$X_L$ protein inhibitor is administered before or concurrently with the JAK2 inhibitor.

Exemplary BCL-$X_L$ protein inhibitors that can be used in the disclosed methods include without limitation ABT-737, ABT-263, ABT-199, Genasense, obatoclax, and combinations thereof.

In nineteenth aspect, the disclosure encompasses a method of predicting the response of a subject to a JAK2 inhibitor-based therapy. The method includes the steps of obtaining a biological sample from the subject and determining the activation state of the AKT and/or ERK pathway in the subject. The presence of an activated AKT and/or ERK pathway is indicative of JAK2 inhibitor-based therapy resistance.

In a twentieth aspect, the disclosure encompasses a method of predicting the response of a subject to a JAK2 inhibitor-based therapy. The method includes the steps of obtaining a biological sample from the subject and determining the activation state of at least one BAD protein and/or BCL-$X_L$ protein. The presence of phosphorylated BAD protein and/or activated BCL-$X_L$ protein is indicative of JAK2 inhibitor-based therapy resistance.

In some embodiments of these methods, the biological sample is taken before, during, or after therapy.

Other objects, features and advantages of the present invention will become apparent after review of the specification, claims and drawings.

DETAILED DESCRIPTION OF THE DISCLOSURE

Figure 1:
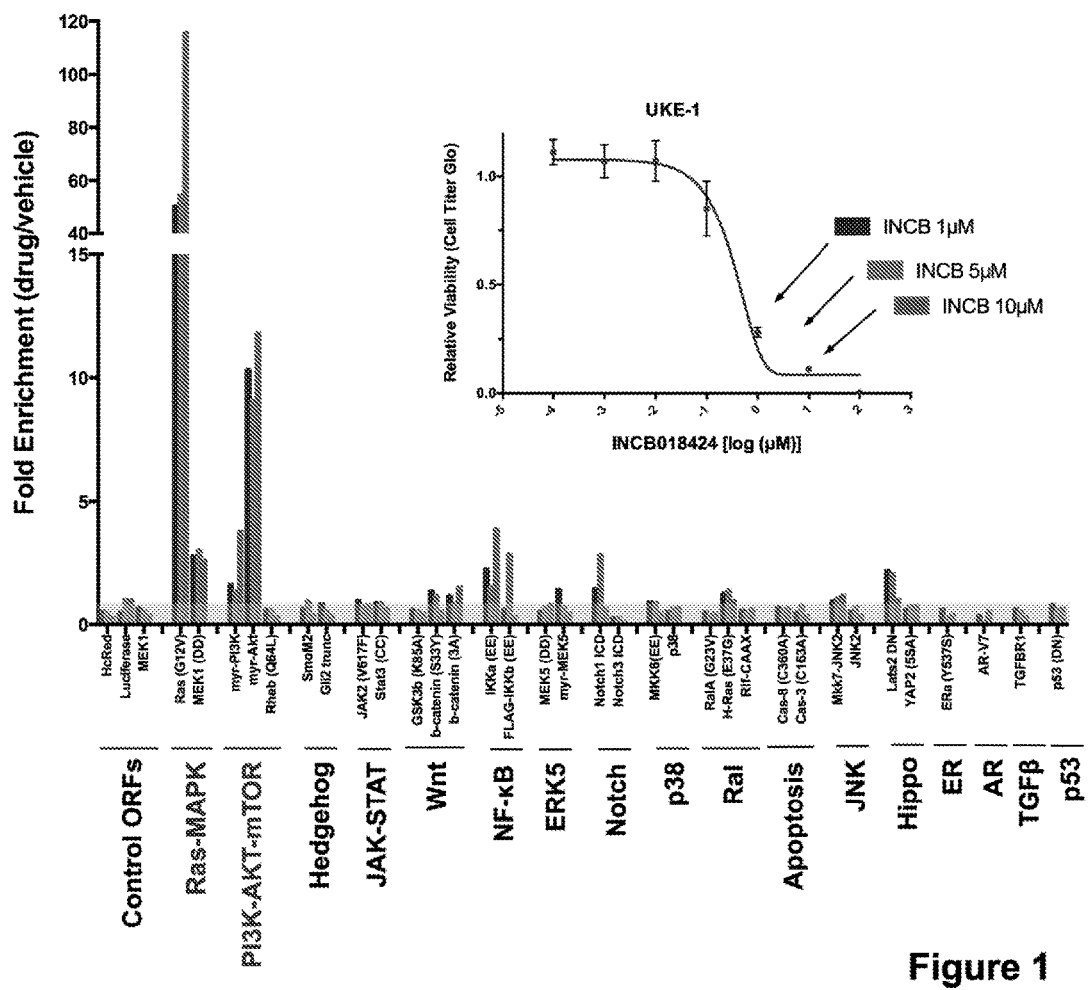
FIG. 1. Pathway activating ORF screen reveals potential modes of resistance to JAK inhibition. UKE-1 cells ($JAK2^{V617F}$) were transduced with a pooled lentiviral library and cultured in the presence of three different lethal concentrations of INCB018424 (inset) or vehicle. Bars show the relative representation of each construct in the drug- vs. vehicle-treated samples; horizontal transparent grey bar indicates a fold enrichment score of 1.0. A full list of the constructs used in this library is available in Table 1.

Before the present materials and methods are described, it is understood that this disclosure is not limited to the particular methodology, protocols, materials, and reagents described, as these may vary. It is also to be understood that the terminology used herein is for the purpose of describing particular embodiments only, and is not intended to limit the scope of the present invention, which will be limited only by the claims.

As used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs.

Definitions

As used herein, the term "administering" refers to bringing a subject, tissue, organ or cells in contact with one or more of the inhibitors described in this disclosure. In certain embodiments, the present invention encompasses administering the compounds useful in the present invention to a patient or subject.

As used herein, the term "cancer" refers to any of those diseases characterized by an uncontrolled division and growth of abnormal cells in the body. Examples include, but are not limited to, myeloproliferative disorders such as polycythemia vera (PCV), essential thrombocythemia (ET), primary myelofibrosis (PMF), chronic eosinophilic leukemia (CEL), chronic myelomonocytic leukemia (CMML), systemic mastocytosis (SM) and idiopathic myelofibrosis (IMF); leukemia such as myeloid leukemia including chronic myeloid leukemia (CML), imatinib-resistant forms of CML, acute myeloid leukemia (AML), and a subtype of AML, acute megakaryoblastic leukemia (AMKL); lymphoproliferative diseases such as myeloma; cancer such as cancer of the head and neck, prostate cancer, breast cancer, ovarian cancer, melanoma, lung cancers, brain tumors, pancreatic cancer and renal cancer. In some embodiments, the cancer comprises a JAK2$^{V617F}$ mutation.

"About" is used to provide flexibility to a numerical range endpoint by providing that a given value may be "slightly above" or "slightly below" the endpoint without affecting the desired result.

As used herein, "treatment," "therapy" and/or "therapy regimen" refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition. For example, treatments for cancers may include the use of anti-cancer/chemotherapeutic agents (e.g., anti-metabolites (e.g., 5-fluoro-uracil, methotrexate, fludarabine), antimicrotubule agents (e.g., vinca alkaloids such as vincristine, vinblastine; taxanes such as paclitaxel, docetaxel), alkylating agents (e.g., cyclophosphamide, melphalan, carmustine, nitrosoureas such as bischloroethylnitrosurea and hydroxyurea), platinum agents (e.g. cisplatin, carboplatin, oxaliplatin, JM-216 or satraplatin, CI-973), anthracyclines (e.g., doxrubicin, daunorubicin), antitumor antibiotics (e.g., mitomycin, idarubicin, adriamycin, daunomycin), topoisomerase inhibitors (e.g., etoposide, camptothecins), anti-angiogenesis agents (e.g. Sutent™ and Bevacizumab) or any other cytotoxic agents, (estramustine phosphate, prednimustine), hormones or hormone agonists, antagonists, partial agonists or partial antagonists, kinase inhibitors, etc.) radiation treatment, surgery and combinations thereof. In certain embodiments, cancers comprising a JAK2$^{V617F}$ mutation may include, but are not limited to, treatment with drugs that inhibit JAK2 activity (e.g., INCB018424). Such treatments are well known and particular to the patient and can be readily determined by one skilled in the art.

The term "effective amount" or "therapeutically effective amount" refers to an amount sufficient to effect beneficial or desirable biological and/or clinical results. The specific "effective amount" will, obviously, vary with such factors as the particular condition being treated, the physical condition of the patient, the duration of the treatment, the nature of concurrent therapy (if any), and the specific formulations employed. The optimum effective amounts can be readily determined by one of ordinary skill in the art using routine experimentation.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. Preferably, the subject is a human patient that is at for, or suffering from, a cancer.

The term "biological sample" as used herein includes, but is not limited to, a sample containing tissues, cells, and/or biological fluids isolated from a subject. Examples of biological samples include, but are not limited to, tissues, cells, biopsies, blood, lymph, serum, plasma, urine, saliva, mucus and tears. In one embodiment, the biological sample is a blood sample (such as a plasma sample) or biopsy sample (such as a tissue/cell sample). In some embodiments, the biological sample comprises cells. In certain embodiments, the biological sample comprises blood. A biological sample may be obtained directly from a subject (e.g., by blood or tissue sampling) or from a third party (e.g., received from an intermediary, such as a healthcare provider or lab technician). In some embodiments, the biological sample is taken before, during, and/or after the administration of the JAK2 inhibitor-based therapy.

A "JAK2 inhibitor," as used herein, includes any compound that disrupts JAK2 production and or the JAK/STAT signaling pathway. Cytokines play key roles in controlling cell growth and the immune response. Many cytokines function by binding to, and activating cytokine receptors found on the cell surface. These receptors in turn rely on the Janus kinase (JAK) family of enzymes for signal transduction. Specifically, Janus kinases phosphorylate activated cytokine receptors which in turn recruit STAT transcription factors that modulate gene transcription. Hence, JAK inhibitors, and specifically JAK2 inhibitors, block cytokine signaling. Examples of JAK2 inhibitors include, but are not limited to, INCB018424 (also known as Ruxolitinib), Tofacitinub, Baricitnib, CYT387, Lestaurtinib, Pacritinib, TG101348 and the like.

An "AKT and/or PI3K inhibitor," as used herein, includes any compound that disrupts AKT production/activity, PI3K production/activity, and or the AKT/PI3K signaling pathway. Examples of AKT1 inhibitors include, but are not limited to, AZD5363, VQD-002, Perifosine, Wortmannin, demthozyviridin, LY294002, CAL101, PX-866, IPI-145, BAY 80-6946, BEX235, RP6503, TGR 1202, SF1126, INK1117, GDC-0941, BKM120, XL147, XL765, Palomid 529, GSK1059615, ZSTK474, PWT33597, 1C87114, TG100-115, CAL263, RP6530, PI-103, GNE-477, CUDC-907, AEZS-136, combinations thereof, and the like.

An "ERK/MEK inhibitor," as used herein, includes any compound that disrupts mitogen-activated protein kinase enzymes (MEK1 and/or MEK2) or ERK production and or the MEK/ERK signaling pathway. The MEK signaling pathway is a chain of proteins in a cell that communicate a signal from a receptor on the cell surface to the DNA in the nucleus. MEK1 and MEK2 function by phosphorylating proteins in the Ras-Raf-MEK-ERK signaling pathway, thereby turning the pathway "on" and "off." When one of the proteins is mutated, it can be stuck in the "on" or "off" position, thereby leading to the development of cancer. Examples of MEK inhibitors include, but are not limited to, Trametinib, Selumetinib, MEK162, PD-325901, XL518, CI-1040, PD035901 and the like.

As used herein, the term "BCL-family inhibitor" includes any inhibitor capable of disrupting or inhibiting the anti-apoptotic proteins of the BCL signaling pathway. The BCL signaling pathway governs mitochondrial outer membrane permeabilization and can be either pro-apoptotic (includes family members Bax, BAD, Bak, and Bok among others) or anti-apoptotic (including Bcl-2, Bcl-xL, and Bcl-w, among others). Examples of such inhibitors include, but are not limited to, ABT-737, ABT-263, ABT-199, Genasense, obatoclax, and combinations thereof.

As used herein, the term "in combination" refers to the use of more than one therapeutic agent (e.g., a JAK2 inhibitor and a BLC-family inhibitor or an AKT and/or PI3K inhibitor and/or MEK inhibitor). The use of the term "in combination" does not restrict the order in which said therapeutic agents are administered to a subject with a disease or disorder, e.g., a cancer.

DETAILED DESCRIPTION

Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the disclosure. All references cited in this specification are to be taken as indicative of the level of skill in the art. Nothing herein is to be construed as an admission that the invention is not entitled to antedate such disclosure by virtue of prior invention.

Provided herein are methods of predicting the response of a subject to a JAK2 inhibitor-based therapy. Further provided are methods for sensitizing and/or reversing resistance to JAK2 inhibitor-based therapy.

Accordingly, one method of the present disclosure provides a method of predicting the response of a subject to a JAK2 inhibitor-based therapy comprising, consisting of, or consisting essentially of obtaining a biological sample from the subject and determining the activation state of the AKT and/or ERK pathway, wherein the presence of an activated AKT and/or ERK pathway is indicative of JAK2 inhibitor-based therapy resistance.

Another method of the present disclosure provides a method of predicting the response of a subject to a JAK2 inhibitor-based therapy comprising, consisting of, or consisting essentially of obtaining a biological sample from the subject and determining the activation state of at least one BAD protein and/or BCL-$X_L$ protein, wherein the presence of phosphorylated BAD protein and/or activated BCL-$X_L$ protein is indicative of JAK2 inhibitor-based therapy resistance.

In some embodiments, the method further comprises determining the presence of AKT and/or ERK pathway activation. In other embodiments, the method further comprises determining the presence of phosphorylated BAD protein and/or activated BCL-$X_L$ protein.

Some of the disclosed methods can be particularly effective at treating subjects whose cancer has become "drug resistant" or "multi-drug resistant." A cancer which initially responded to an anti-cancer drug, such as a JAK2 inhibitor, becomes resistant to that anti-cancer drug when the anti-cancer drug is no longer effective in treating the subject with the cancer. For example, many tumors will initially respond to treatment with an anti-cancer drug by decreasing in size or even going into remission, only to develop resistance to the drug. "Drug resistant" tumors are characterized by a resumption of their growth and/or reappearance after having seemingly gone into remission, despite the administration of increased dosages of the anti-cancer drug. Cancers that have developed resistance to two or more anti-cancer drugs are said to be "multi-drug resistant." For example, it is common for cancers to become resistant to three or more anti-cancer agents, often five or more anti-cancer agents and at times ten or more anti-cancer agents.

As detailed below in the Example, the inventors have found possible mechanisms of JAK2 inhibitor therapy resistance in once sensitive cells. These mechanisms include the activation in AKT and/or H-Ras activity and phosphorylation of BAD and/or activated BCL-$X_L$ proteins that allow for the reactivation of pro-survival pathways that were once inhibited by the JAK2 inhibitor. Targeting these mechanisms has therapeutic value.

Accordingly, another aspect of the present disclosure provides a method of sensitizing a subject to a JAK2 inhibitor wherein the subject has developed resistance to a JAK2 inhibitor-based therapy and has an activated AKT pathway comprising, consisting of, or consisting essentially of administering to the subject a therapeutically effective amount of an AKT and/or PI3K inhibitor in combination with the JAK2 inhibitor.

Another aspect of the resent disclosure provides a method of reversing resistance to JAK2 inhibitor therapy in a subject wherein the subject has an activated AKT pathway comprising, consisting of, or consisting essentially of administering to the subject a therapeutically effective amount of an AKT and/or PI3K inhibitor in combination with the JAK2 inhibitor.

In some embodiments, the AKT and/or PI3K inhibitor is administered before or concurrently with the JAK2 inhibitor.

Another aspect of the present disclosure provides a method of sensitizing a subject to a JAK2 inhibitor wherein the subject has developed resistance to a JAK2 inhibitor-based therapy and has an activated ERK pathway comprising administering to the subject a therapeutically effective amount of an ERK/MEK inhibitor in combination with the JAK2 inhibitor.

Yet another aspect of the present disclosure provides a method of reversing resistance to JAK2 inhibitor therapy in a subject wherein the subject has an activated ERK/MEK pathway comprising, consisting of, or consisting essentially of administering to the subject a therapeutically effective amount of an ERK/MEK inhibitor in combination with the JAK2 inhibitor.

In some embodiments, the ERK/MEK inhibitor is administered before or concurrently with the JAK2 inhibitor.

There are certain cases where there is coincident AKT and ERK activation. One mechanism by which this can be achieved is through activation of Ras oncogenes, hence co-targeting the AKT and ERK pathways may be beneficial. Accordingly, another aspect of the present disclosure provides a method of sensitizing a subject to a JAK2 inhibitor wherein the subject has developed resistant to a JAK2 inhibitor-based therapy and has an activated AKT and ERK pathway comprising, consisting of, or consisting essentially of administering to the subject a therapeutically effective amount of an AKT and/or PI3K inhibitor and an ERK/MEK inhibitor in combination with the JAK2 inhibitor.

Yet another aspect of the present disclosure provides a method of reversing resistance to JAK2 inhibitor therapy in a subject wherein the subject has an activated AKT and ERK/MEK pathway comprising, consisting of, or consisting essentially of administering to the subject a therapeutically effective amount of an AKT and/or PI3K inhibitor and an ERK/MEK inhibitor in combination with the JAK2 inhibitor.

In some embodiments, the AKT and/or PI3K inhibitor and the ERK/MEK inhibitor are administered before or concurrently with the JAK2 inhibitor.

Another aspect of the present disclosure provides a method of sensitizing a subject to a JAK2 inhibitor wherein the subject has developed resistance to a JAK2 inhibitor-based therapy and has at least one phosphorylated BAD protein and/or activated BCL-$X_L$ protein comprising, consisting of, or consisting essentially of administering to the subject a therapeutically effective amount of a BCL-$X_L$ protein inhibitor in combination with the JAK2 inhibitor.

Another aspect of the present disclosure provides a method of reversing resistance to JAK2 inhibitor therapy in a subject wherein the subject has at least one phosphorylated BAD- and/or activated BCL-$X_L$ protein comprising, consisting of, or consisting essentially of administering to the subject a therapeutically effective amount of a BCL-$X_L$ protein inhibitor.

BCL-$X_L$ protein inhibitors have a beneficial therapeutic effect even in the absence of the a JAK2 inhibitor in these resistant cancer cells. Accordingly, another aspect of the present disclosure provides a method of treating a subject having resistance to JAK2 inhibitor therapy and at least one phosphorylated BAD protein and/or activated BCL-$X_L$ protein comprising, consisting of, or consisting essentially of administering to the subject a therapeutically effective amount of a BCL-$X_L$ protein inhibitor.

In preferred embodiments, the BCL-family inhibitor or the AKT and/or PI3K and/or MEK inhibitor is administered prior to, or concurrently with, the JAK2 inhibitor. In such embodiments, a first inhibitor, such as a BCL-family inhibitor or an AKT and/or PI3K and/or MEK inhibitor, can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before) or concomitantly with the administration of a JAK2 inhibitor to a subject with a disease or disorder, e.g. a proliferative disorder, such as cancer.

In one embodiment, the BCL-family inhibitor or the AKT and/or PI3K and/or MEK inhibitor and the JAK2 inhibitor are dosed on independent schedules. In another embodiment, the BCL-family inhibitor or the AKT and/or PI3K inhibitor and/or the MEK inhibitor and the JAK2 inhibitor are dosed on approximately the same schedule. In another embodiment, the BCL-family inhibitor or the AKT and/or PI3K and/or MEK inhibitor and the JAK2 inhibitor are dosed concurrently or sequentially on the same day.

The disclosure also provides pharmaceutical compositions comprising one or more of the disclosed inhibitors in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. It is also envisioned that the compounds of the present invention may be incorporated into transdermal patches designed to deliver the appropriate amount of the drug in a continuous fashion.

For preparing solid compositions such as tablets, the principal active ingredient is mixed with a pharmaceutically acceptable carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture for a compound of the present invention, or a pharmaceutically acceptable salt thereof. When referring to these preformulation compositions as homogeneous, it is meant that the active ingredient is dispersed evenly throughout the composition so that the composition may be easily subdivided into equally effective unit dosage forms such as tablets, pills and capsules. This solid pre-formulation composition is then subdivided into unit dosage forms of the type described above containing from 0.1 to about 500 mg of the active ingredient of the present invention. Typical unit dosage forms contain from 1 to 100 mg, for example, 1, 2, 5, 10, 25, 50 or 100 mg, of the active ingredient. The tablets or pills can be coated or otherwise compounded to provide a dosage affording the advantage of prolonged action. For example, the tablet or pill can comprise an inner dosage and an outer dosage component, the latter being in the form of an envelope over the former. The two components can be separated by an enteric layer which, serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

The following examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

EXAMPLE

Example 1: Ras Effector Pathways Drive Resistance to JAK Inhibitors by Suppressing BAD-Mediated Apoptosis Abstract.

The recent discovery that myeloproliferative neoplasms (MPNs) depend on constitutive JAK-STAT signaling through the frequently mutated $JAK2^{V617F}$ allele suggests that targeting this pathway may yield clinical benefit. In MPN patients, JAK inhibitor therapy improves splenomegaly and systemic symptoms but does not appreciably reduce the clonal burden. To identify potential mechanisms underlying this resistance phenomenon, we performed pathway-centric gain-of-function screens which revealed that the activation of Ras or its effector pathways Akt and ERK renders cells insensitive to JAK inhibition. We found that resistant MPN cells could be fully resensitized to JAK inhibitors via co-inhibition of the Akt and ERK pathways. Mechanistically, the survival of normally proliferating $JAK2^{V617F}$ cells is controlled by JAK2-mediated inactivating phosphorylation of the pro-apoptotic protein BAD. Upon JAK inhibitor treatment in sensitive cells, BAD is dephosphorylated, allowing it to bind and sequester the pro-survival protein $BCL-X_L$, triggering apoptosis. Ras effector pathways drive resistance by maintaining BAD phosphorylation in the presence of JAK inhibitors, yielding a specific dependence on $BCL-X_L$ for survival. Indeed, $BCL-X_L$ inhibitors potently induce apoptosis in JAK inhibitor-resistant cells. Notably, activating mutations in Ras commonly co-occur with $JAK2^{V617F}$ mutations in MPN patients, suggesting that Ras effector pathways likely play an important role in the resistance observed in patients. Taken together, these results demonstrate that the JAK2/BAD/$BCL-X_L$ survival axis in $JAK2^{V617F}$ cells can be co-opted by Ras effector pathways to drive resistance, and that resistance can be overcome by either combined inhibition of JAK and Ras effector pathways or by direct $BCL-X_L$ inhibition.

Introduction

In 2005, a recurrent somatic point mutation in the pseudokinase domain of the Janus kinase 2 gene (JAK2) was discovered in a large proportion of patients with myeloproliferative neoplasms (MPNs,(1-3)), a class of hematologic malignancies arising from hematopoietic progenitors that includes acute and chronic myeloid leukaemias, polycythaemia vera, essential thrombocythaemia and primary myelofibrosis. The prevalence of the $JAK2^{V617F}$ mutation and the subsequent finding that these malignancies are dependent upon constitutive JAK/STAT signaling prompted strong interest in targeting JAK2 in these patients, leading to the development of several JAK kinase inhibitors such as TG101348 (SAR302503), INCB018424 (Ruxolitinib), and CYT387 (4-6). In clinical studies, JAK inhibitors were found to produce palliative effects associated with decreased inflammatory cytokine abundance and reduced splenomegaly but were unable to reverse the disease by decreasing the malignant clone burden (7,8).

The inability of JAK inhibitor therapy to reduce or eliminate the MPN clone may be caused by a number of factors, including: (i) second site mutations in the JAK2 kinase domain which block effective drug binding to its target (9); (ii) the reactivation of JAK-STAT signaling in the presence of JAK inhibitors, for example through the heterodimerization of JAK2 with JAK1 or TYK2, (10); and (iii) the activation of compensatory signaling pathways which enable malignant cells to circumvent the toxic effects of JAK inhibition. Informative studies were recently conducted to examine options (i) and (II) above, indicating that these mechanisms may contribute to the resistance observed in some patients. However, despite considerable evidence that compensatory signaling pathways can contribute to resistance to anticancer drugs, including kinase targeted therapies (11-14), no studies have systematically assessed the potential roles of such pathways in the resistance of MPNs to JAK inhibitors.

To identify potential compensatory pathways, we performed pooled gain-of-function lentiviral screens using a recently developed open reading frame (ORF) expression library containing activating mutants representing key nodes in 17 major signaling pathways frequently implicated in oncogenesis and drug resistance. By constitutively activating individual signaling pathways in cancer cells and then culturing those cells in the presence of lethal doses of drugs, this method makes it is possible to identify those pathways whose activation has the potential to confer a survival advantage (14).

Using this strategy, we found that activation of Ras and its effector pathways, particularly Akt, renders cells insensitive to JAK inhibitors by blocking drug-induced apoptosis. These pathways are mutationally activated in a subset of JAK2$^{V617F}$ MPN patients, and the inhibition of Ras effector pathways converts JAK inhibitor-resistant cell lines to a JAK inhibitor-sensitive state. Finally, by resolving the mechanism of drug-induced apoptosis and its rescue by Ras effectors, we uncover new therapeutic strategies for JAK inhibitor refractory disease.

Results.

Ras Effector Pathways are Capable of Conferring Resistance to JAK Inhibition.

Activators of 17 oncogenic signaling pathways (Table 1) were screened in JAK2$^{V617F}$ UKE-1 cells to identify those capable of driving resistance to INCB018424 (INCB). Screens were performed using low multiplicity of infection (MOI) conditions to ensure that only a single transgene pathway activator was introduced into each cell. Further, a moderate strength promoter (PGK) was used to minimize the likelihood of superphysiological pathway activation owing to overexpression (15).

TABLE 1

List of pathway-activating constructs and controls

| Pathway | ID | Construct | Source | Official symbol and NM# | C-terminal V5 tag? | Functionally validated? | Functional Validation Method |
|---|---|---|---|---|---|---|---|
| Ras-MAPK | A2 | Ras (G12V) | David Sabatini Lab, MIT/HHMI/WIBR | HRAS NM_005343.2 - human variant 1 | − | Yes | Western (P-ERK) |
| | A3 | MEK1 (S218D, S222D) | David Sabatini Lab, MIT/HHMI/WIBR | MAP2K1 NM_002755.3 - human | +/− | Yes (both +/− V5) | Western (P-ERK) |
| P13K-AKT-mTOR | B1 | myr-FLAG-PIK3CA | addgene 10889 | PIK3CA NM_174574.1 - bovine | − | Yes | Western (P-AKT) |
| | B2 | myr-FLAG-AKT1 | addgene 15294 | AKT1 NM_005163.2 - human variant 1 | − | Yes | Western (P-AKT, P-S6K1) |
| | B3 | FLAG-Rheb (Q64L) | addgene 21050 | RHEB NM_005614.3 - human | − | Yes | Western (P-S6K1) |
| NF-κB | C1 | IKKα (S176E, S180E) | Michael Karin Lab, UCSD | CHUK NM_001278.3 - human | + | Yes | Reporter (NF-κB_Luc) |
| | C2 | FLAG-IKKβ (S177E, S181E) | addgene 11105 | IKBKB NM_001556.2 - human variant 1 | − | Yes | Reporter (NF-κB_Luc) |
| Jak/Stat | D1 | JAK2 (V617F) | William Vainchecker Lab, Institut Gustave Roussy | JAK2 NM_004972.3 - human | + | Yes | Reporter (Stat_Luc) |
| | D2 | Stat3 (A662C, N664C, V667L) | addgene 24983 | STAT3 NM_139276.2 - human variant 1 | + | Yes | Reporter (Stat_Luc) |
| Wnt/b-catenin | E1 | β-catenin (S33A, S37A, T41A, S45A) | addgene 14717 | Ctnnb1 NM_001165902.1 - mouse variant 2 | +/− | Yes (both +/− V5) | Reporter (TCF-LEF_Luc) |
| | E2 | GSK3β (K85A) | addgene 14755 | GSK3B NM_001146156.1 - human variant 2 | + | Yes | Reporter (TCF-LEF_Luc) |
| | E3 | β-catenin (S33Y) | addgene 16519 | CTNNB1 NM_001904.3 - human variant 1 | +/− | Yes (both +/− V5) | Reporter (TCF-LEF_Luc) |
| JNK | F1 | JNK2 WT O/E (MAPK9) | David Sabatini Lab, MIT/HHMI/WIBR | MAPK9 NM_002752.4 - human variant JNK2-a2 | + | No | Reporter (AP1_Luc) |
| | F2 | Mkk7-JNK2 fusion | addgene 19727 | Map2k7 NM_011944.3 linker MAPK9 NM_002752.4 mouse Mkk7 variant 2 plus human variant JNK2-a2 | − | Yes | Reporter (AP1_Luc) |
| ERK5 | G1 | MEK5 DD (S311D, T315D) | Axel Ullrich lab, MPIB | MAP2K5 NM_145160.2 - human variant 1 | + | No | Western (ERK5 laddering) |
| | G2 | myr-FLAG-MEK5 | addgene 20514 | MAP2K5 NM_145160.2 - human variant 1 | − | Yes | Western (ERK5 laddering) |

TABLE 1-continued

List of pathway-activating constructs and controls

| Pathway | ID | Construct | Source | Official symbol and NM# | C-terminal V5 tag? | Functionally validated? | Functional Validation Method |
|---|---|---|---|---|---|---|---|
| Notch | H1 | Notch1 intracellular domain | addgene 17623 | NOTCH1 NM_017617.3 - human, intracellular domain see sequence | +/− | Yes (both +/− V5) | Reporter (HES1_Luc) |
|  | H2 | Notch3 intracellular domain | addgene 26894 | NOTCH3 NM_000435.2 - human, intracellular domain see sequence | +/− | Yes (both +/− V5) | Reporter (HES1_Luc) |
| p38 | I1 | p38 WT O/E (MAPK14) | David Sabatini Lab, MIT/ HHMI/WIBR | MAPK14 NM_139012.2 - human variant 2 | + | Yes | Western (P-p38) |
|  | I2 | FLAG-MKK6 (S207E, T211E) | addgene 13518 | MAP2K6 NM_002758.3 - human | − | Yes | Western (P-p38) |
| Hedgehog | J1 | Gli2 truncation | addgene 17649 | GLI2 NM_005270.4 - human, truncation mutant see sequence | + | Yes | Reporter (Gli_Luc) |
|  | J2 | SmoM2 (W535L) | addgene 14016 (with site-directed mutagenesis) (*Nature*, 2009, 458: 776-9) | SMO NM_005631.4 - human | + | Yes | Reporter (Gli_Luc) |
| TGFβ apoptosis (extrinsic pathway) | K1 | TGFβR1 | addgene 19162 | TGFBR1 NM_004612.2 - human variant 1 | + | Yes | Immunofluorescence (P-Smad2/3) |
| All apoptosis | N1 | Caspase-3 (C163A) | addgene 11814 | CASP3 NM_032991.2 - human variant beta | + | Yes | Western (cleaved caspase 3/7) |
| Estrogen receptor | O1 | ERα (Y537S mutant) | Benita Katzenellen bogen Lab, UIUC | ESR1 NM_000125.3 - human variant 1 | + | Yes | Reporter (ERE_Luc) |
| Androgen receptor | P1 | AR-V7 | Charles Sawyers Lab, MSK/HHMI | AR NM_000044.3 - human variant 1, splice isoform see sequence | +/− | Yes (both +/− V5) | Western (ARE_Luc) |
| Hippo | Q1 | FLAG-YAP2 (5SA) | addgene 27371 | YAP1 NM_001195044.1 - human variant 3 | − | Yes | Immunofluorescence (nuclear YAP) |
|  | Q2 | Lats2 kinase dead (K697R) | cloned directly from HepG2 cDNA (with site-directed mutagenesis) | LATS2 NM_014572.2 - human | +/− | Yes (both +/− V5) | Immunofluorescence (nuclear YAP) |
| p53 | R1 | p53 (dominant negative R175H mutant) | addgene 16436 | TP53 NM_001126114.2 - human variant 3 | + | Yes | Reporter (p53_Luc) |
| Ral | S1 | HRas (G12V, E37G) | addgene 18745 | HRAS NM_001130442.1 - human variant 3 | +/− | Not tested |  |
|  | S2 | Rgl2-CAAX | addgene 12592 | Rgl2 NM_009059.2 - mouse plus C-term KRAS | + | Not tested |  |
|  | S3 | RalA (G23V) (two forms - full and mature peptide) | addgene 15252 | RALA NM_005402.3 - human | +/− | Not tested |  |
| CONTROLS | X1 | HcRed | addgene 25892 | N/A | +/− | N/A |  |
|  | X2 | Luciferase | addgene 25894 | N/A | +/− | N/A |  |
|  | X3 | MEK1 | David Sabatini Lab, MIT/ HHMI/WIBR | MAP2K1 NM_002755.3 - human | + | N/A |  |

Figure 2:
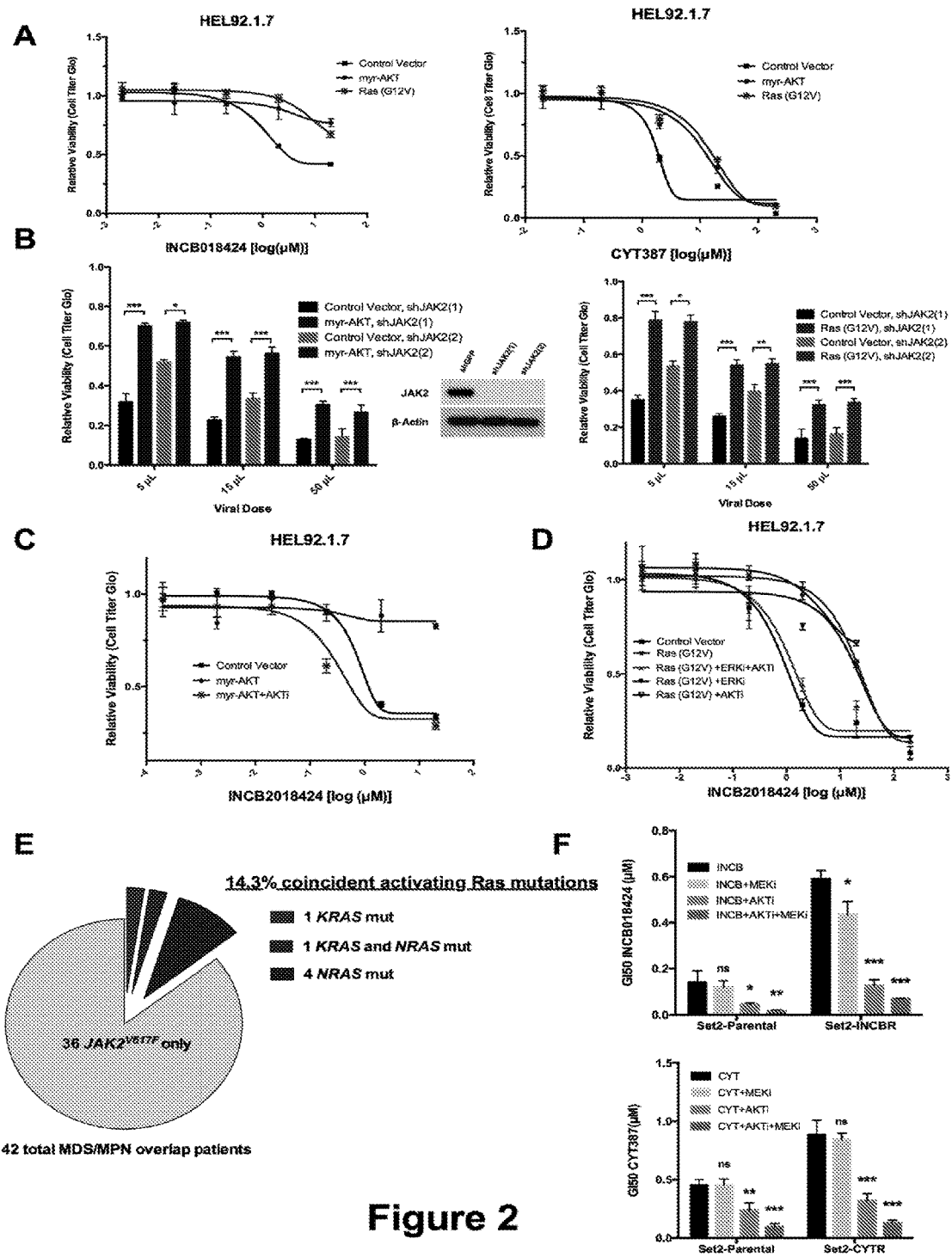
FIG. 2. The Ras effector pathways Akt and ERK drive resistance to JAK inhibitors. (A) HEL92.1.7 cells expressing the indicated ORFs were treated with the indicated concentrations of INCB018424 and CYT387. Cell viability was measured using Cell Titer Glo. Error bars represent the SD of three replicate experiments. (B) The relative viability of either control or pathway-active HEL92.1.7 cells is shown after transduction with two independent JAK2 hairpins at three viral doses. Error bars indicate SEM of three replicate experiments. (C) Relative proliferation of HEL92.1.7 cells expressing the indicated ORFs and treated with INCB alone or in combination with MK2206 (AKTi); error bars as in (A). (D) Similar to (C) except cells are treated with INCB alone, INCB with VX-11E (ERKi), INCB with MK2206 (AKTi), or INCB with both; error bars as in (A). (E) Forty-two $JAK2^{V617F}$ positive MDS/MPN overlap patients were analyzed for coincident Ras mutations. (F) GI50 values were calculated for Set2-parental cells and those with evolved resistance to either INCB (INCBR; top) or CYT (CYTR; bottom). GI50 values for the respective JAK inhibitors were measured alone or in combination with AKTi, MEKi (AZD6244) or AKTi plus MEKi. Error bars indicate SD of three replicate experiments. *p<0.05, p<0.01, *p<0.001 by Student's t test. Staurosporine inhibits PrkA in vitro phosphorylation in a dose-dependent manner. Autophosphorylation (arrow) and myelin basic protein (MBP) phosporylation (*) activity was assayed for PrkA (lanes 1-5), Lmo0618 (lanes 6-9), and S.a.Stk1 (lanes 10-11) in the presence or absence of 1 μM, 10 μM or 100 μM staurosporine.
Figure 3:
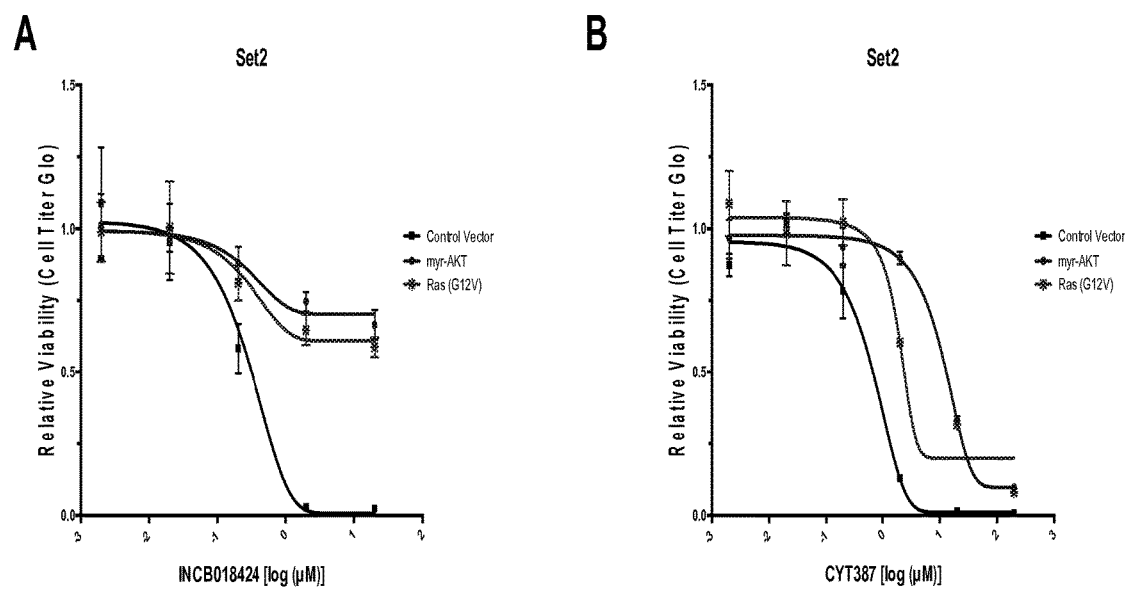
FIG. 3. Ras effector pathway activation confers resistance to JAK inhibition in an additional $JAK2^{V617F}$ positive cell line, Set2. (A) Relative proliferation of Set2 cells transduced with the indicated constructs and treated with the indicated concentrations of INCB. Error bars show the SD of three replicate experiments. (B) Same as in (A) except cells were treated with CYT.

Two constructs—myristolated-Akt and RasG12V—scored as strong hits (FIG. 1). It was notable that these constructs were consistently enriched in the screens by greater than 10- and 50-fold, respectively, as our recent study involving 110 similar drug modifier screens spanning diverse drugs and cancer types found that enrichment of a hit by greater than 10-fold is rare (14). In eight point GI50 validation assays, Akt and Ras activation resulted in 10- to 50-fold shifts in the GI50 concentrations of two different JAK inhibitors (INCB and CYT387 (CYT)) in two additional JAK2V617F positive cell lines (HEL92.1.7 and Set2), thus confirming the potential of these pathways to drive resistance when hyperactivated (FIG. 2A and FIG. 3).

Figure 4:
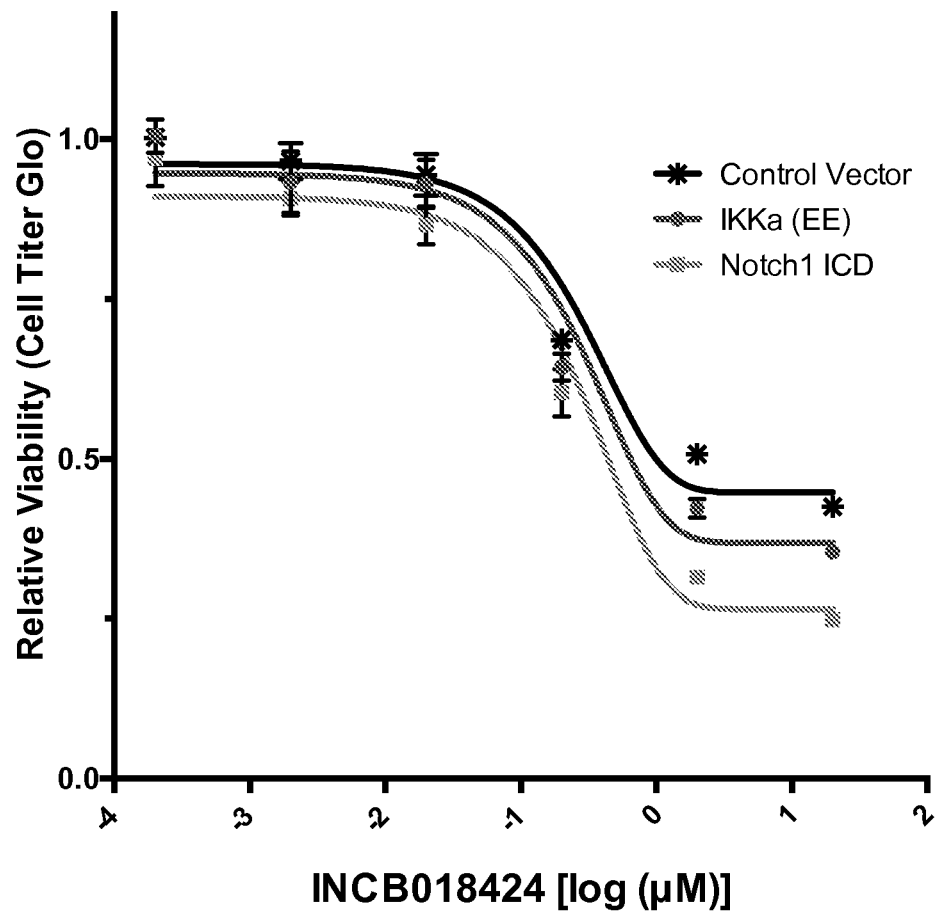
FIG. 4. Weak-scoring constructs from the primary screen—IKKα and Notch1—do not confer resistance to JAK inhibition in secondary GI50 assays. HEL92.1.7 cells were transduced with the indicated constructs and treated with the indicated concentrations of INCB. Error bars show the SD of three replicate experiments.

Separately, Akt and Ras activation also conferred resistance to the direct knockdown of JAK2 by two independent shJAK2 constructs (FIG. 2B), suggesting that, unlike the recently reported JAK2-JAK1/JAK2-Tyk2 heterodimerization phenomenon (10), Akt- and Ras-driven resistance can operate independently of JAK2 expression. Note that constructs from the NF-κB and Notch pathways also scored weakly in the primary screen (~3 fold enrichment; FIG. 1) but failed to confer robust resistance to INCB in subsequent GI50 validation assays (FIG. 4).

Ras Effector Pathways Drive Resistance in JAK Inhibitor-Resistant Cells.

Figure 5:
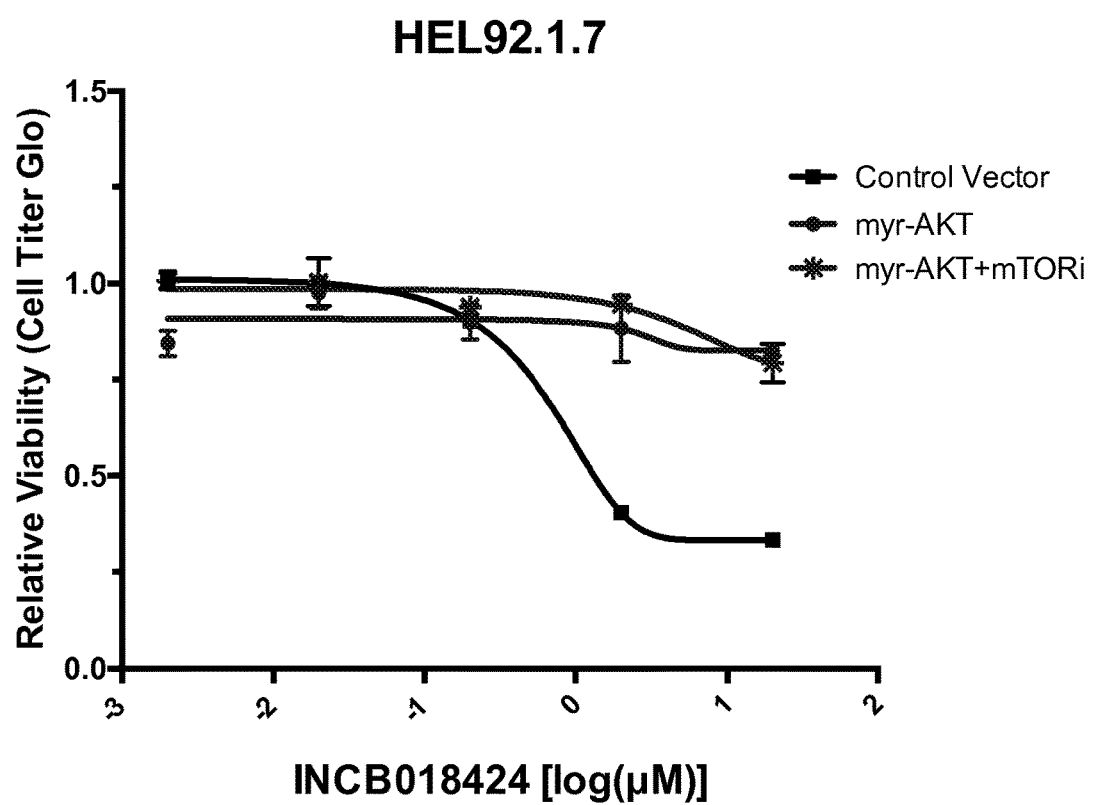
FIG. 5. Akt-mediated resistance to JAK inhibition occurs independently of downstream mTOR activity. HEL92.1.7 cells were transduced with the indicated constructs and treated with the indicated concentrations of INCB, alone or in combination with a dual PI3K/mTOR inhibitor (BEZ-235). Error bars show the SD of three replicate experiments.

Both Akt and Ras constructs are activators of Ras effector pathways, a diverse set of pathways that have been implicated extensively in cell growth and survival processes downstream of activated Ras (16). To better understand which particular effector pathways control Akt- and Ras-driven resistance, we sought to reverse resistance in these cells using small molecule pathway inhibitors. Akt-expressing cells could be fully resensitized to INCB using an allosteric Akt inhibitor, MK-2206 (FIG. 2C), but not by using BEZ-235, a dual PI3K/mTOR inhibitor, suggesting that resistance in these cells does not depend on Akt-mediated mTOR activation (FIG. 5). Ras-expressing cells could be resensitized by dual inhibition of the ERK and Akt effector pathways (using the ERK inhibitor VX-11E and MK-2206, respectively), but not by inhibition of either pathway alone, suggesting that Ras-driven resistance involves the concerted activation of these two effector pathways (FIG. 2D).

To investigate the potential clinical relevance of JAK inhibitor resistance driven by Ras effector pathways, we first queried a cohort of JAK2$^{V617F}$ positive MDS/MPN patients for coincident activating mutations in KRAS or NRAS (Table 2).

TABLE 2

Patient cohort information

| Exam No | Gender 1 = female; 2 = male) | Age (years) | Leukocytes/ μL | Hemoglobin g/dL | Thrombocytes/ μL | disease state | disease |
|---|---|---|---|---|---|---|---|
| 05-001643 | 2 | 83.5 | 24,000 | 10.2 | 41,000 | Follow-up | CMML |
| 08-001661 | 1 | 68 | 129,200 | 10.7 | 50,000 | primary diagnosis | CMML |
| 08-003092 | 2 | 80.7 | 21,500 | 12.3 | 220,000 | primary diagnosis | CMML |
| 08-004139 | 2 | 74.8 | 19,500 | 12.4 | 432,000 | primary diagnosis | CMML |
| 08-012014 | 2 | 72.5 | 15,600 | | | primary diagnosis | CMML |
| 08-012254 | 2 | 76.3 | 10,500 | | | Follow-up | CMML |
| 08-015947 | 2 | 78 | 10,200 | 11.0 | 406,000 | primary diagnosis | CMML |
| 08-018102 | 2 | 74.2 | 3,600 | 8.9 | 74,000 | primary diagnosis | CMML |
| 08-026363 | 1 | 75.1 | 20,900 | 7.7 | 212,000 | primary diagnosis | CMML |
| 09-003889 | 1 | 84 | 15,600 | 12.1 | 295,000 | primary diagnosis | CMML |
| 09-004402 | 2 | 66 | 39,000 | 9.6 | 10,000 | primary diagnosis | CMML |
| 10-015859 | 2 | 72.1 | 24,500 | 15.5 | 355,000 | primary diagnosis | CMML |
| 10-030238 | 2 | 80.3 | 7,800 | 9.1 | 149,000 | primary diagnosis | CMML |
| 13-000919 | 2 | 66.1 | | | | primary diagnosis | CMML |
| 13-017640 | 2 | 82.1 | 6,850 | 12.0 | 134,000 | primary diagnosis | CMML |
| 13-023089 | 2 | 77.9 | 37,620 | 8.3 | 321,000 | primary diagnosis | CMML |
| 10-031747 | 2 | 65.6 | 19,390 | 16.1 | 319,200 | primary diagnosis | MDS/MPN overlap |
| 13-017518 | 1 | 58 | 2,700 | 9.4 | 599,000 | primary diagnosis | MDS/MPN overlap |
| 05-001444 | 1 | 76 | 21,450 | 12.6 | 638,000 | primary diagnosis | MPN |
| 07-001074 | 2 | 80.8 | 19,800 | 17.2 | 480,000 | primary diagnosis | MPN |
| 07-003690 | 1 | 68.3 | 16,000 | 15.0 | 600,000 | primary diagnosis | MPN |
| 08-023331 | 1 | 61 | 10,500 | 14.0 | 672,000 | primary diagnosis | MPN |
| 10-029143 | 1 | 84.5 | 4,900 | 14.5 | 343,000 | primary diagnosis | MPN |
| 13-027823 | 2 | 75.8 | 11,000 | 11.8 | 897,000 | primary diagnosis | MPN |
| 07-019117 | 1 | 76.8 | 10,800 | 9.9 | 963,000 | primary diagnosis | RARS-T |
| 08-004644 | 1 | 75.9 | 4,600 | 7.5 | 691,000 | primary diagnosis | RARS-T |
| 08-010296 | 2 | 72 | 4,900 | 10.2 | 986,000 | Follow-up | RARS-T |
| 08-021722 | 2 | 79.1 | 12,900 | 12.0 | 680,000 | primary diagnosis | RARS-T |
| 09-015841 | 2 | 74 | 4,180 | 8.3 | 473,000 | primary diagnosis | RARS-T |
| 09-017730 | 1 | 89.1 | 19,960 | 9.7 | 916,000 | primary diagnosis | RARS-T |
| 09-032026 | 2 | 63.5 | 6,300 | 12.2 | 534,000 | primary diagnosis | RARS-T |
| 10-009701 | 1 | 58.1 | 14,800 | 11.7 | 525,000 | primary diagnosis | RARS-T |
| 10-012914 | 2 | 81 | 6,300 | 8.7 | 572,000 | primary diagnosis | RARS-T |
| 10-031268 | 2 | 74.9 | 10,700 | 13.1 | 690,000 | primary diagnosis | RARS-T |
| 11-009704 | 2 | 81 | 7,280 | 10.7 | 487,000 | primary diagnosis | RARS-T |
| 11-018299 | 1 | 84.3 | 9,500 | 11.3 | 925,000 | primary diagnosis | RARS-T |
| 11-026860 | 2 | 85.5 | 10,200 | 7.7 | 553,000 | primary diagnosis | RARS-T |
| 11-044024 | 1 | 60.3 | 4,600 | 6.9 | 572,000 | primary diagnosis | RARS-T |
| 12-000368 | 2 | 55.3 | 8,100 | 8.9 | 850,000 | primary diagnosis | RARS-T |

TABLE 2-continued

Patient cohort information

| | | | | | | | |
|---|---|---|---|---|---|---|---|
| 12-030867 | 2 | 76.3 | 6,000 | 9.4 | 497,000 | primary diagnosis | RARS-T |
| 12-034168 | 1 | 77.5 | 12,800 | 11.2 | 1,069,000 | primary diagnosis | RARS-T |
| 13-000358 | 2 | 75.9 | 14,500 | 11.2 | 990,000 | primary diagnosis | RARS-T |

| Exam No | Death (0 = alive; 1 = dead) | OS (in days) | JAK2V617F | KRAS mutation | KRAS sequence | KRAS % mutated | NRAS mutation | NRAS sequence | NRAS % mutated |
|---|---|---|---|---|---|---|---|---|---|
| 05-001643 | | | 1 | 1 | p.Gly12Arg | 1.6 | 1 | p.Gly12Asp(+) Gly12Cys | 2.0 + 15.0 |
| 08-001661 | 0 | 35 | 1 | 0 | | | 1 | p.Gly13Asp | 39.0 |
| 08-003092 | 1 | 133 | 1 | 0 | | | 0 | | |
| 08-004139 | 0 | 1746 | 1 | 0 | | | 1 | p.Thr58Ile | 8.0 |
| 08-012014 | | | 1 | 0 | | | 0 | | |
| 08-012254 | | | 1 | 0 | | | 0 | | |
| 08-015947 | 1 | 179 | 1 | 0 | | | 0 | | |
| 08-018102 | 1 | 55 | 1 | 0 | | | 0 | | |
| 08-026363 | 1 | 78 | 1 | 0 | | | 0 | | |
| 09-003889 | | | 1 | 0 | | | 1 | p.Gly12Asp | 31.0 |
| 09-004402 | 0 | 30 | 1 | 0 | | | 1 | p.Gly13Asp | 13.0 |
| 10-015859 | 0 | 457 | 1 | 0 | | | 0 | | |
| 10-030238 | | | 1 | 0 | | | 0 | | |
| 13-000919 | | | 1 | 0 | | | 0 | | |
| 13-017640 | | | 1 | 0 | | | 0 | | |
| 13-023089 | | | 1 | 0 | | | 0 | | |
| 10-031747 | | | 1 | 0 | | | 0 | | |
| 13-017518 | | | 1 | 0 | | | 0 | | |
| 05-001444 | | | 1 | 0 | | | 0 | | |
| 07-001074 | | | 1 | 0 | | | 0 | | |
| 07-003690 | | | 1 | 0 | | | 0 | | |
| 08-023331 | | | 1 | 0 | | | 0 | | |
| 10-029143 | 0 | 3937 | 1 | 0 | | | 0 | | |
| 13-027823 | | | 1 | 0 | | | 0 | | |
| 07-019117 | 0 | 181 | 1 | 0 | | | 0 | | |
| 08-004644 | 0 | 1636 | 1 | 0 | | | 0 | | |
| 08-010296 | | | 1 | 0 | | | 0 | | |
| 08-021722 | 1 | 1211 | 1 | 0 | | | 0 | | |
| 09-015841 | 0 | 365 | 1 | 0 | | | 0 | | |
| 09-017730 | 0 | 946 | 1 | 0 | | | 0 | | |
| 09-032026 | 0 | 1125 | 1 | 0 | | | 0 | | |
| 10-009701 | 0 | 1153 | 1 | 0 | | | 0 | | |
| 10-012914 | 1 | 605 | 1 | 0 | | | 0 | | |
| 10-031268 | 0 | 447 | 1 | 0 | | | 0 | | |
| 11-009704 | 0 | 299 | 1 | 0 | | | 0 | | |
| 11-018299 | 0 | 590 | 1 | 0 | | | 0 | | |
| 11-026860 | 0 | 349 | 1 | 0 | | | 0 | | |
| 11-044024 | | | 1 | 0 | | | 0 | | |
| 12-000368 | | | 1 | 0 | | | 0 | | |
| 12-030867 | | | 1 | 0 | | | 0 | | |
| 12-034168 | | | 1 | 0 | | | 0 | | |
| 13-000358 | | | 1 | 1 | p.Asp33Glu | 10.0 | 0 | | |

In a cohort of 42 treatment naïve patients, six (14.3%) carried canonical activating mutations in either KRAS or NRAS, including one patient with activating mutations in both (FIG. 2E). In a second set of experiments, we obtained JAK2$^{V617F}$ Set2 cells that were evolved to a resistant state by chronic exposure to JAK inhibitors CYT (Set2-CYTR) and INCB (Set2-INCBR) (10). As expected, Set2-CYTR and Set2-INCBR cells were resistant to JAK inhibition by GI50 assay relative to Set2-Parental cells (FIG. 2F). Akt inhibition using MK-2206 resensitized both Set2-CYTR and Set2-INCBR cells to parental GI50 values, and co-inhibition of both the Akt and ERK effector pathways (the latter using the mitogen-activated protein kinase 1 and 2 (MEK1/2) inhibitor AZD-6244) further sensitized both resistant and parental cells.

Taken together, these data establish that (i) Ras or Ras effector pathway activation can confer considerable resistance to JAK inhibitors, (ii) JAK2$^{V617F}$ positive patients frequently carry activating mutations in Ras genes sufficient to drive Ras effector signaling, and (iii) resistance in both engineered and evolved JAK inhibitor-resistant cell lines can be reversed by inhibition of the Akt or Akt+MEK or ERK Ras effector pathways.

Figure 6:
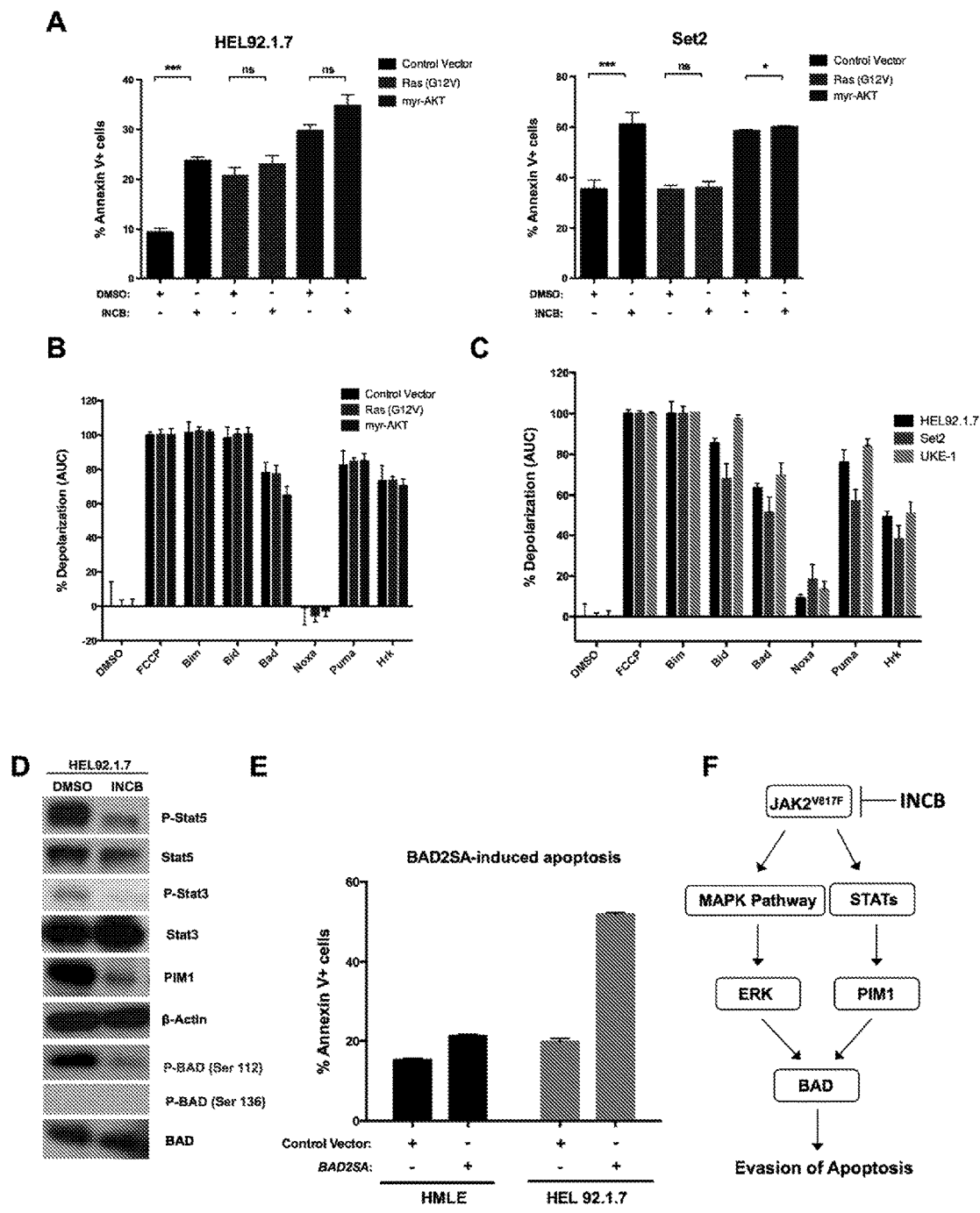
FIG. 6. Ras effector pathway activation rescues JAK inhibitor-induced apoptosis and BH3-profiling suggests BAD as a key gatekeeper to apoptosis in $JAK2^{V617F}$ positive cells. (A) HEL92.1.7 and Set2 cells were transduced with the indicated constructs, treated with INCB, and stained with 7AAD and Annexin V to measure apoptosis at 72 and 24 hours post drug treatment, respectively. Error bars indicate SD of three replicate experiments. (B) Digitonin-permeabilized HEL92.1.7 cells transduced with the indicated constructs were stained with the mitochondrial potential-sensitive JC1 dye and treated with a panel of BH3 peptides. Percent depolarization is shown as the area under the curve (AUC) normalized to positive control fully depolarized mitochondria (FCCP). DMSO serves as the negative control. Data shown are representative of three independent experiments for each cell line derivative. (C) Same as in (B) except in this case the indicated $JAK2^{V617F}$ positive cell lines were profiled to query their apoptotic dependencies. (D) Lysates from HEL92.1.7 cells were immunoblotted as indicated after treatment with INCB for 6 hours. Blots are representative of three replicate experiments. (E) Twenty-four hours after transduction with the indicated ORFs, HMLE and HEL92.1.7 cells were stained with 7AAD and Annexin V to measure induction of apoptosis. Error bars indicate SD of three replicate experiments. (F) A model depicting the putative signaling axis downstream of mutant JAK2. ***p<0.001 by Student's t test.

JAK Inhibitor-Induced Apoptosis is Normally Stimulated by BAD in JAK2$^{V617F}$ Cells Whereas parental JAK2$^{V617F}$ cells appear to undergo significant cell death following INCB treatment, cells expressing Ras or Akt do not, suggesting that resistance may involve the suppression of apoptosis. By Annexin-V staining, INCB treatment induces apoptosis in multiple JAK2$^{V617F}$ cell lines, but apoptosis induction is abrogated in the context of Ras effector activation (FIG. 6A). To gain potential insight into the molecular regulation of apoptosis in JAK2$^{V617F}$ cells, we performed BH3 profiling (17-19). In this assay, cells are permeabilized, stained with a mitochondrial-potential sensitive dye, and treated with peptides derived from the BH3 domains of pro-apoptotic BH3-only proteins. BH3 peptides can bind and inactivate specific anti-apoptotic proteins, triggering mitochondrial outer membrane permeabilization (MOMP) and mitochondrial depolarization in cells dependent on those proteins. BH3 profiling can measure overall priming for apoptosis (20) or identify dependence on specific anti-apoptotic proteins.

Figure 7:
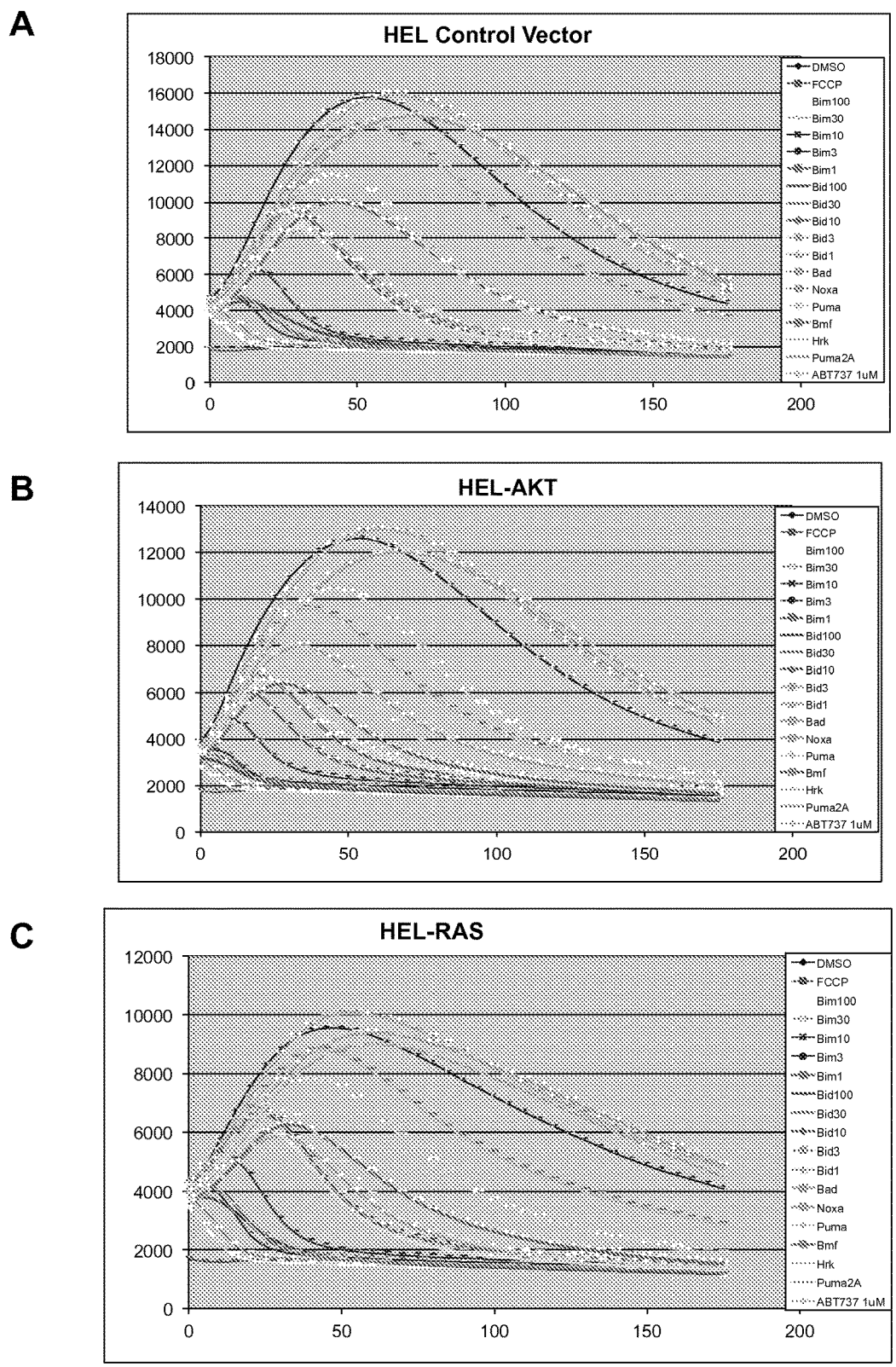
FIG. 7. BH3 profiling of HEL92.1.7 derivatives show similar mitochondrial priming that is independent of JAK inhibitor sensitivity. (A-C) Digitonin-permeabilized HEL92.1.7 cells transduced with the indicated constructs were stained with the mitochondrial potential-sensitive JC1 dye, incubated with a panel of BH3 peptides at the indicated concentrations, and mitochondrial potential was measured over a 180 minute time period. Mitochondrial priming profiles were generated for HEL control (A), Akt (B), and Ras (C) expressing cells. Data shown are representative of three independent experiments for each cell line derivative.

In this Example, mitochondria in parental and resistant cells were equally primed for apoptosis as evidenced by extensive depolarization induced by the BIM, BID and PUMA peptides, which can bind and inactivate all of the major anti-apoptotic proteins. Interestingly, the cells were also depolarized by the BAD (binds BCL-2 and BCL-$X_L$) and HRK (binds BCL-$X_L$ only) peptides which indicates a potential dependence specifically on BCL-$X_L$ for survival (18, 21) (FIG. 6B and FIG. 7). We then profiled all three lines (HEL92.1.7, Set2, and UKE-1), confirming that this pattern is consistent across JAK2$^{V617F}$ cells (FIG. 6C).

Figure 8:
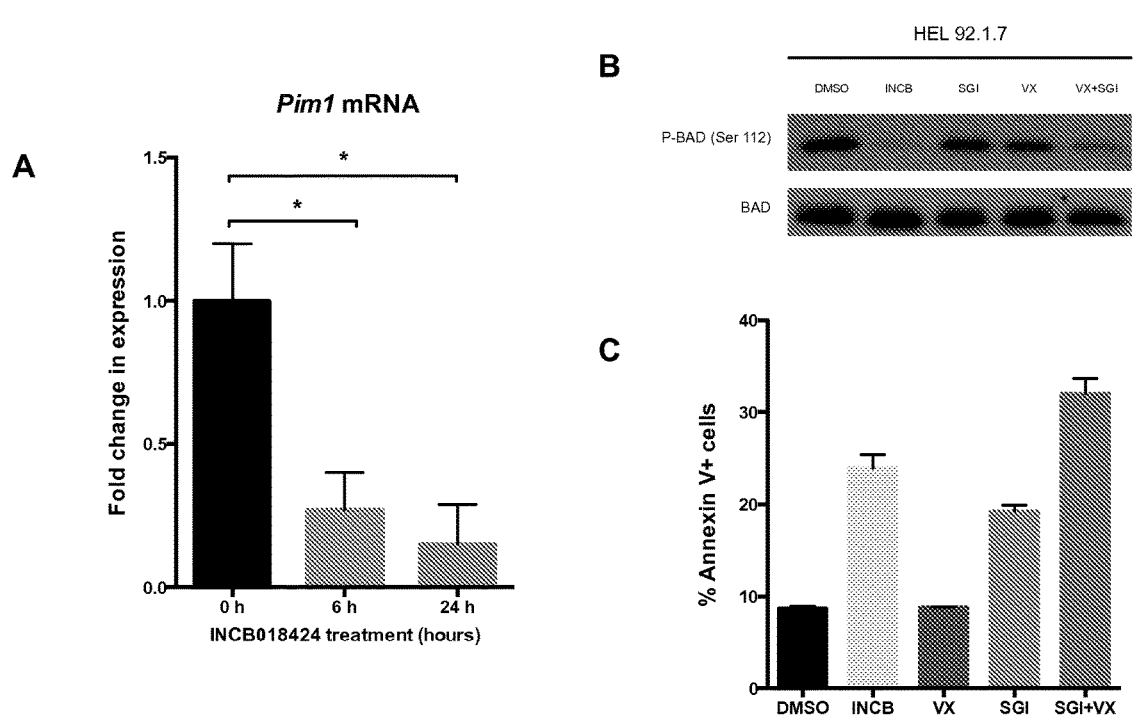
FIG. 8. PIM1 and ERK phosphorylate BAD at $Ser^{112}$ downstream of JAK/STAT signaling and influence subsequent entrance into apoptosis. (A) Quantification of the change in Pim1 mRNA expression in HEL92.1.7 cells treated with INCB for the indicated time. Error bars indicate the SEM for three replicates. (B) After treatment with the indicated drugs, protein lysates were harvested from HEL92.1.7 cells and probed using the antibodies shown. Blots are representative of three replicate experiments. (C) HEL92.1.7 cells were treated with INCB, SGI-1776, VX-11E, or the combination for 72 hours and then stained with 7AAD and Annexin V to measure the induction of apoptosis. Error bars show SEM of three replicate experiments. *p<0.05, by Student's t test.

Interestingly, the pro-apoptotic function of BAD is known to be inhibited by phosphorylation at either Ser$^{112}$ or Ser$^{136}$ by a number of kinases (22-25). Two of these kinases, PIM1 and ERK, which both phosphorylate BAD at Ser$^{112}$ (23, 25, 26) are stimulated by JAK/STAT signaling (10, 27). Consistent with this, we found that PIM1 expression is inhibited by JAK2 inhibition (FIG. 6D and FIG. 8A). Additionally, to effectively phenocopy the reduction of phospho-BAD at Ser$^{12}$ conferred by JAK inhibition, it is necessary to inhibit both ERK and PIM1 (FIG. 8B). Further, in apoptosis assays, ERK inhibition alone has no detectable affect, while PIM1 inhibition induces apoptosis, but to a lesser extent than direct JAK inhibition (FIG. 8C). Combined inhibition of PIM1 and ERK yields a greater than additive effect, resulting in amounts of apoptosis higher than that achieved by direct JAK inhibition. These data demonstrate that the relevant BAD kinases in the setting of normally proliferating JAK2$^{V617F}$ cells are likely ERK and PIM1.

Figure 9:
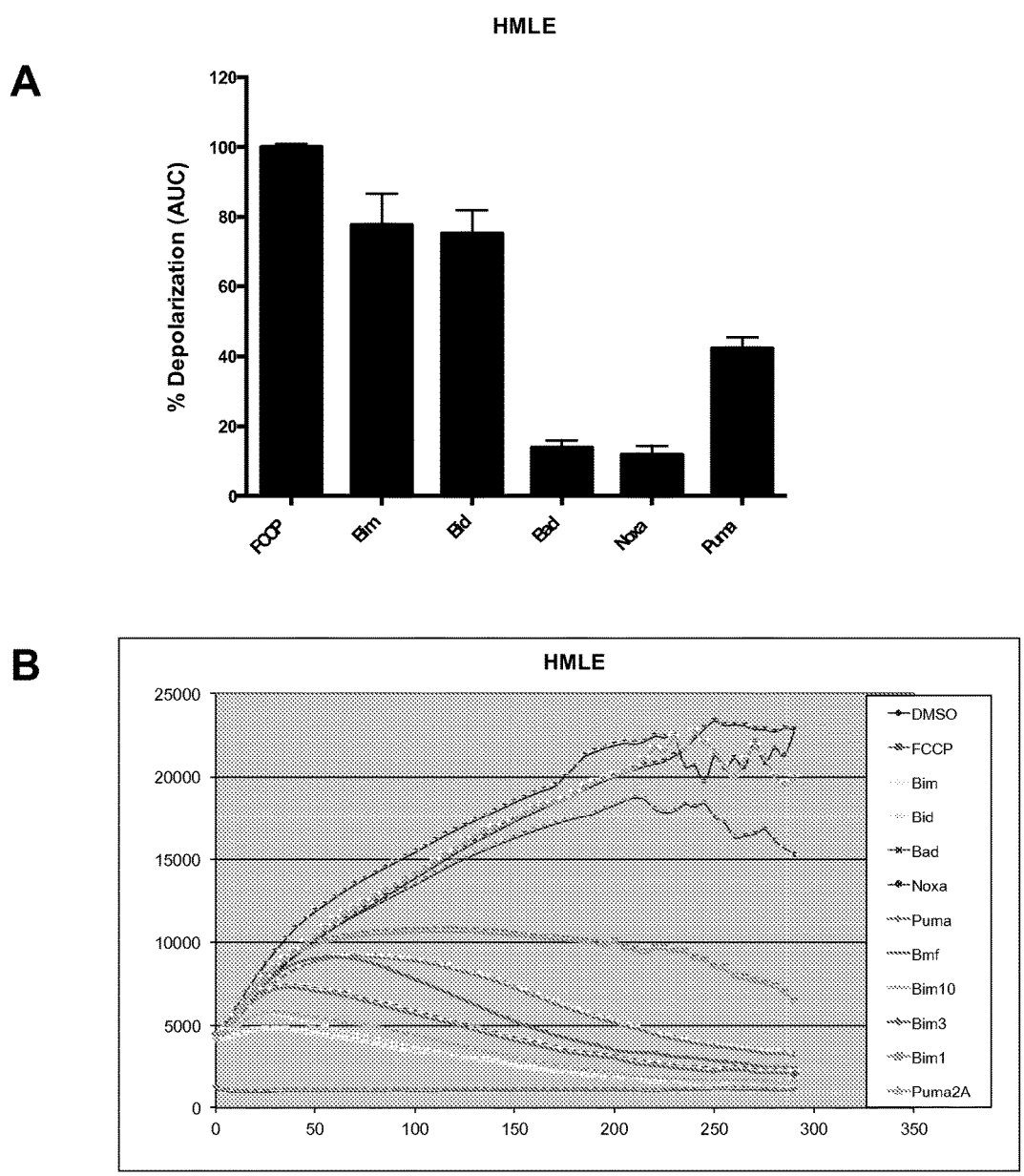
FIG. 9. BH3 profiling indicates that HMLE cells are not depolarized by BAD peptide and thus not dependent on BCL-2/BCL-$X_L$. (A) Similar to FIG. 6B except in HMLE cells. (B) Mitochondrial depolarization over time in HMLE cells, similar to FIG. 7.

To functionally verify that BAD phosphorylation is critical to apoptosis in JAK2$^{V617F}$ cells, we transduced HEL92.1.7 cells with either a double Ser-to-Ala murine BAD mutant, BAD2SA, which cannot be phosphorylated at sites 112 and 136 (22, 23, 28), or a control vector. BAD2SA expression in HEL92.1.7 cells induced apoptosis comparable to JAK or PIM1+ERK inhibition (FIG. 6E), whereas the expression of BAD2SA in HMLE cells, a control cell line that is insensitive to BAD-induced apoptosis, had a negligible effect on apoptosis, as expected (FIG. 6E and FIG. 9). Together, these results support a model wherein BAD phosphorylation inhibits apoptosis and survival downstream of JAK2 and PIM1/ERK in JAK2$^{V617F}$ positive cells (FIG. 6F).

Ras Effector Pathways Drive Resistance by Blocking DAD-Induced Apoptosis.

Figure 10:
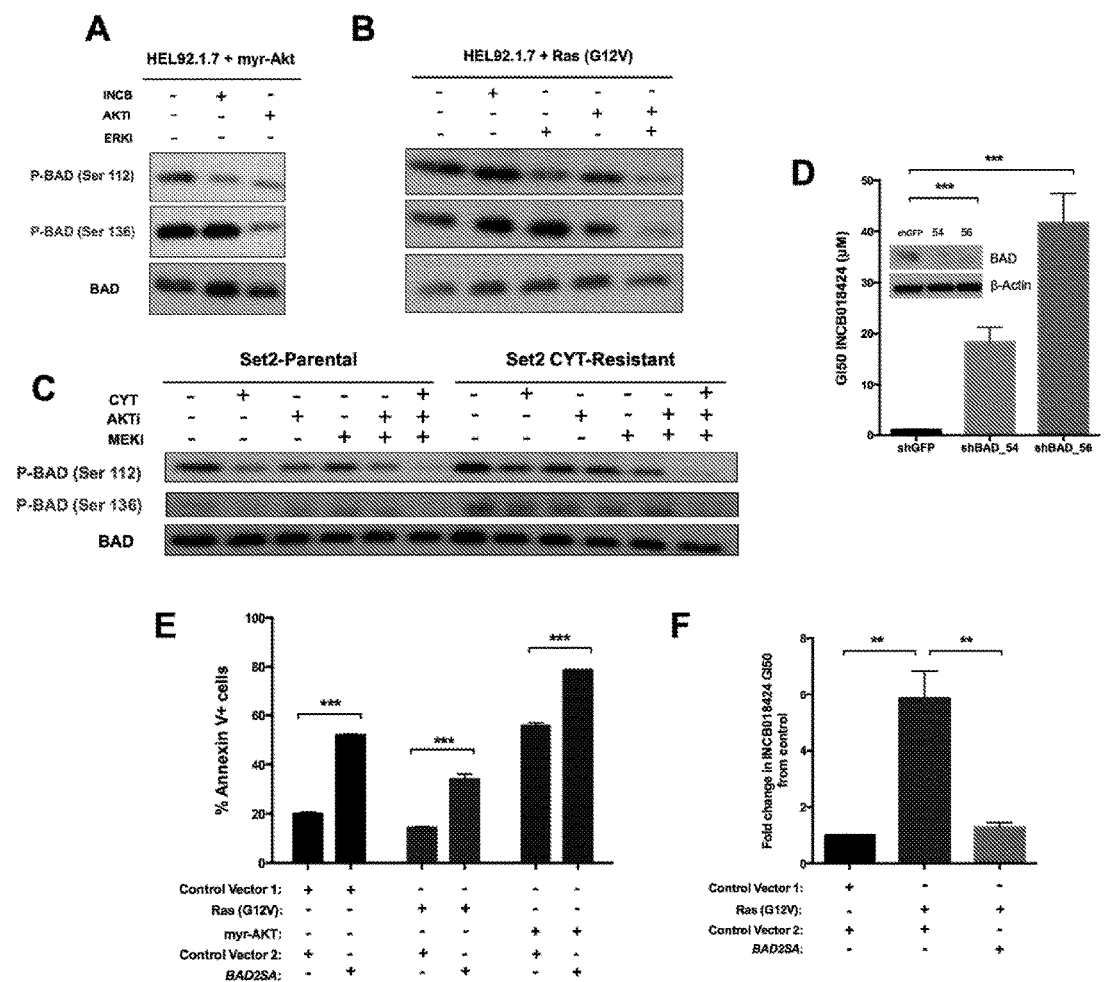
FIG. 10. BAD activity, governed by phosphorylation status at Ser 112 and 136, dictates drug sensitivity and induction of apoptosis in both the drug-sensitive and resistant state. (A-C) After 6 hours of treatment with the specified drugs, protein lysates were prepared from either myr-Akt-transduced HEL92.1.7 (A), Ras (G12V)-transduced HEL92.1.7 (B), Set2-Parental, or Set2-CYTR cells (C) and immunoblotted with the indicated antibodies. Blots are representative of three replicate experiments. (D) INCB GI50 values for HEL92.1.7 cells expressing the indicated short hairpin vectors; protein knockdown assessed 72 hours after lentiviral transduction and selection (inset). (E, F) HEL92.1.7 derivatives stably expressing the indicated ORFs were transduced with a second ORF expressing either a second control vector or BAD2SA. (E) Twenty-four hours after selection, cells were stained with 7AAD and Annexin V to measure the induction of apoptosis. Error bars indicate SD of three replicate experiments. (F) The fold change in INCB GI50 value was calculated for the same HEL92.1.7 derivatives after transduction with the indicated vectors. Error bars indicate SD of three replicate experiments. p<0.01, *p<0.001 by Student's t test.

Activation of the Ras effector pathways Akt and ERK leads to inhibitory phosphorylation of BAD at Ser 136 and 112, respectively, independent of PIM (22, 25). We therefore hypothesized that resistance to JAK inhibition by Ras effector pathways may be mediated through their rescue of BAD phosphorylation. To test this, we examined BAD phosphorylation in Akt- or Ras-expressing cells in the presence of INCB. In Akt-expressing cells, phosphorylation of Ser$^{136}$ was enhanced by Akt activation both in the presence and absence of INCB; this phosphorylation was reversed by treatment with an Akt inhibitor (FIG. 10A). In Ras-expressing cells, Ser 112 and 136 remained phosphorylated in the presence of INCB; this phosphorylation was reversed by combined treatment with Akt and ERK pathway inhibitors (FIG. 10B). Similarly, BAD is phosphorylated at Ser$^{112}$ in Set2-parental cells, where this phosphorylation is sensitive to JAK inhibition. Conversely, in independently evolved Set2-resistant cells, BAD is phosphorylated at both Ser 112 and 136 and these phosphorylation events are insensitive to JAK inhibition. Finally, BAD phosphorylation can be fully abrogated in Set2-resistant cells by combined treatment with JAK, Akt, and ERK pathway inhibitors (FIG. 10C). In sum, these data demonstrate that activation of the Ras effector pathways Akt and ERK rescues inhibitory phosphorylation of BAD in the presence of JAK inhibitors in both engineered and evolved JAK inhibitor-resistant cells.

If inactivating phosphorylation of BAD by Ras effector pathways is responsible for the observed resistance, then knockdown of BAD should also confer resistance independently of Ras activation. Indeed, knockdown of BAD by two independent shRNA constructs confers robust resistance to INCB that phenocopies Ras effector activation, suggesting that resistance is mediated through BAD (FIG. 10D). To further substantiate BAD's role in resistance, we infected Ras- or Akt-expressing cells with BAD2SA and evaluated its effects on apoptosis. For both resistant HEL derivatives, BAD2SA expression alone was sufficient to induce significant apoptosis, similar to the response in the parental cells (FIG. 10E).

Finally, to demonstrate that BAD governs sensitivity to JAK inhibitors downstream of Ras effector pathways, we sought to reverse the resistance seen in Akt- or Ras-expressing cells by co-expression of BAD2SA. In the Akt-active state, cells expressing BAD2SA were unable to survive long enough to complete the GI50 assay, underscoring the importance of BAD in these cells. In the Ras-active state, we were able to preserve a population of BAD2SA-expressing cells. Consistent with a model of resistance driven by inactivating phosphorylation of BAD by Ras effectors, expression of BAD2SA was sufficient to re-sensitize these cells to treatment with JAK inhibitors (FIG. 10F). These findings indicate that resistance to JAK inhibitors driven by Ras effector pathways functions by reactivating inhibitory phosphorylation of BAD downstream of JAK.

BCL-$X_L$ is the Relevant Anti-Apoptotic Target Downstream of JAK and BAD.

BAD can potentially bind and inactivate BCL-2, BCL-$X_L$, and BCL-w (19). HRK is only able to bind BCL-$X_L$. Thus the BH3 profiling results predict that these cells are specifically dependent upon only BCL-$X_L$ (FIG. 6B, C). Immunoblotting of HEL92.1.7 cells show that BCL-$X_L$ is highly expressed compared to the other anti-apoptotic proteins BCL-2 and MCL-1 (FIG. 11A); thus, it might be expected that inhibition of BCL-$X_L$ would be toxic to these cells.

Figure 11:
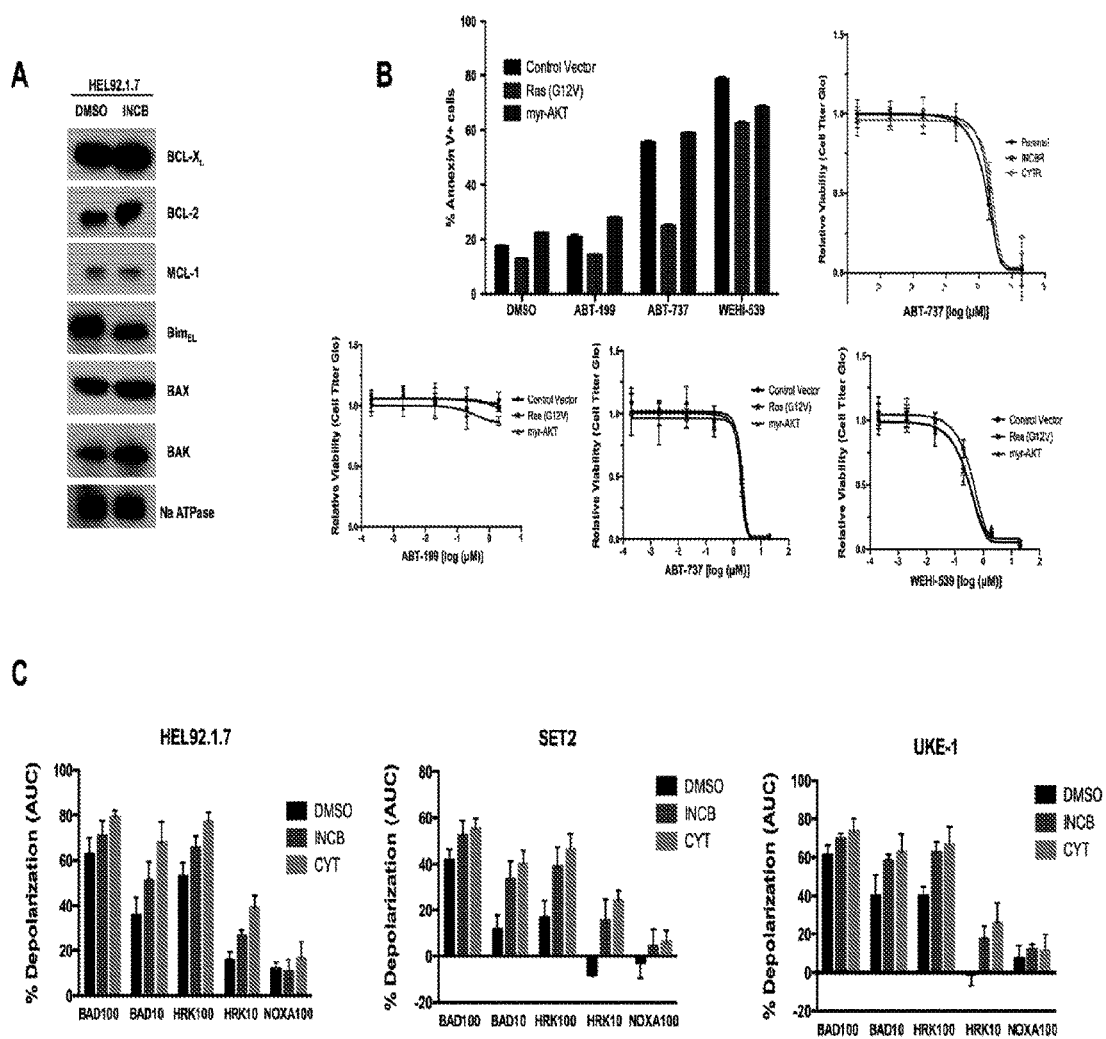
FIG. 11. BCL-$X_L$, not BCL-2 or MCL-1, is the key anti-apoptotic effector downstream of JAK and BAD. (A) HEL92.1.7 cells were treated with INCB for 6 hours and immunoblotted as shown. Blots are representative of three replicate experiments. (B) HEL92.1.7 ORF-expressing derivatives were treated with either a selective BCL-2 inhibitor (ABT-199), a selective BCL-$X_L$ inhibitor (WEHI-539), or BCL-family inhibitor (ABT-737) for 48 hours and then stained with 7AAD and Annexin V to measure the induction of apoptosis. Error bars indicate SEM of three replicate experiments (Below and Right). As in FIG. 2A, the relative proliferation for the indicated HEL92.1.7 derivatives or Set2-Parental, -INCBR, and -CYTR cell lines treated with the specified inhibitors is shown. Error bars indicate SD of three replicate experiments. (C) HEL92.1.7, Set2, and UKE-1 cells were BH3 profiled as before with slight alterations. Cells were incubated with the indicated JAK inhibitors for 8 hours and then profiled using either 100 M or 10 μM of the indicated peptide. Error Bars indicate the SD of three independent experiments for each cell line.
Figure 12:
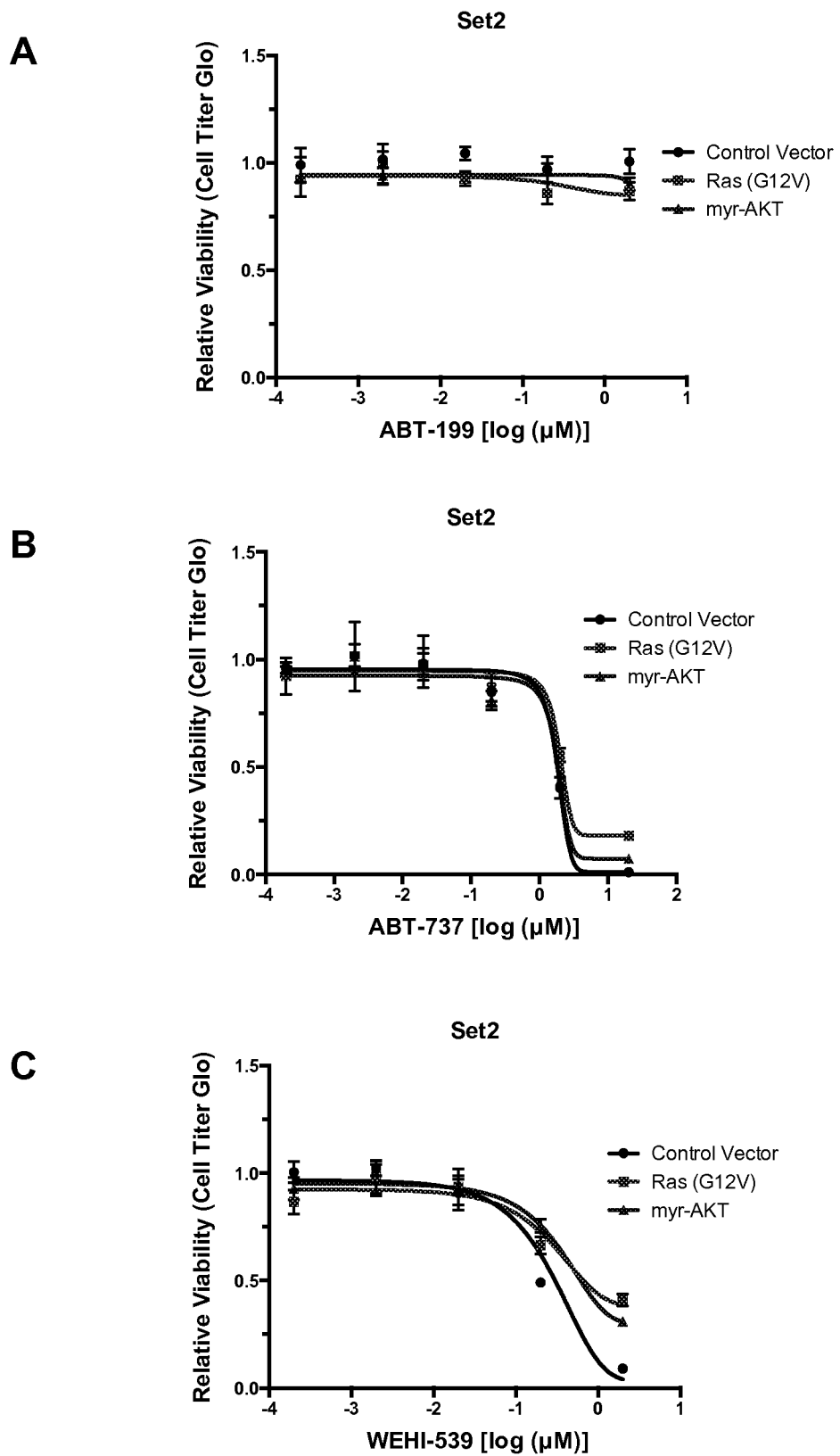
FIG. 12. An additional JAK2$^{V617F}$ positive cell line, Set2, shows sensitivity to inhibition of BCL-$X_L$, but not BCL-2. (A-C) Relative proliferation of Set2 ORF-expressing derivatives were treated with either a selective BCL-2 (ABT-199; A), BCL-family (ABT-737; B), or a selective BCL-$X_L$ (WEHI-539; C) inhibitor. Error bars indicate SD of three replicate experiments.

To test this hypothesis, we measured viability and apoptosis in cells treated with ABT-199 (a selective BCL-2 inhibitor), WEHI-539 (a selective BCL-$X_L$ inhibitor), and ABT-737 (a dual BCL-2/BCL-$X_L$ inhibitor). Parental cells and engineered Ras effector-activated cells were insensitive to ABT-199 but sensitive to both WEHI-539 and ABT-737 (FIG. 11B, FIG. 12). Additionally, independently evolved JAK inhibitor-resistant cells were also equally sensitive to ABT-737 when compared to matched parental cells (FIG. 11B). To confirm this BCL-$X_L$ dependency downstream of JAK signaling, we examined the effects of JAK inhibition on the BH3 profiles of our JAK2$^{V617F}$ positive cells. After incubation with two different JAK inhibitors for 8 hours, all three lines show an increased sensitivity to titrations of both the BAD and HRK peptides (FIG. 11C), suggesting that abrogation of BCL-$X_L$ occurs downstream of JAK inhibition. Importantly, sensitivity to the NOXA peptide (binds only MCL-1) did not appreciably increase, implying little to no role for MCL-1 in this setting. Collectively, these data support a model in which survival in JAK2-driven MPNs relies specifically on the activation state of BAD and its consequent downstream regulation of BCL-$X_L$.

Figure 13:
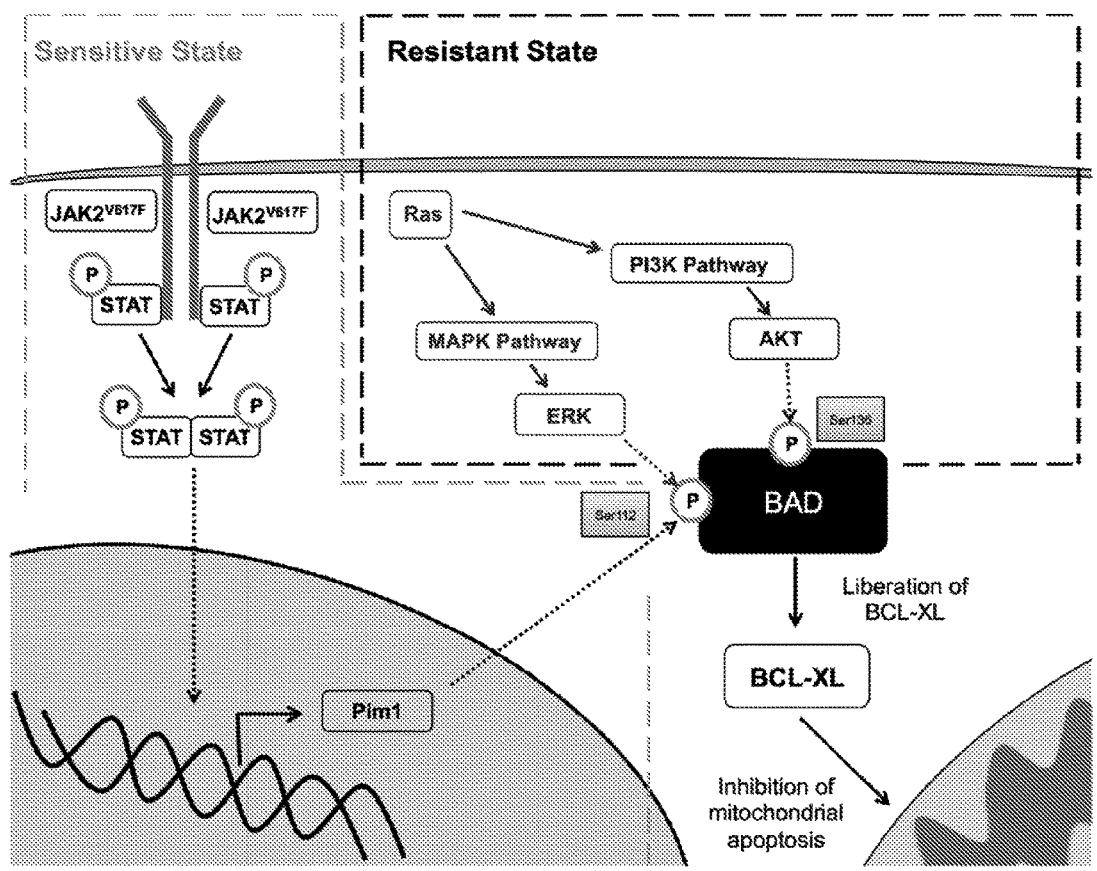
FIG. 13. A BAD/BCL-$X_L$-centric model governing survival in JAK inhibitor-resistant and sensitive cells. In the sensitive state (grey dashed line), survival is predominantly controlled by canonical JAK signaling-mediated inactivation of BAD at the Ser$^{112}$ site. In the resistant state (black dashed line), Ras effector pathways ERK and Akt, driven by activating mutations in Ras or other upstream signals, provide compensatory survival signals at the functionally equivalent Ser 112 and 136 sites, rescuing the effects of JAK2 inhibition and representing a coalescent signaling node through which survival is orchestrated in JAK2$^{V617F}$ cells.

Resistance to JAK inhibition can thus be driven by Ras effector-mediated suppression of the BAD/BCL-$X_L$ signaling axis, and reciprocally, resistance can be inhibited by either co-inhibition of JAK and the Ras effector pathways Akt and ERK or by direct inhibition of BCL-$X_L$ (FIG. 13).

Discussion

Our findings demonstrate that the activation of Ras or its effector pathways Akt and ERK can efficiently rescue JAK inhibitor-driven apoptosis in JAK2$^{V617F}$ MPN cells. Rescue is based on the fact that Ras effector pathways and the JAK2/STAT/PIM pathway can each redundantly phosphorylate and inactivate BAD, the pro-apoptotic protein whose activation status determines survival in these cells. In normally proliferating cells the inhibition of JAK2 leads to dephosphorylation of BAD and its sequestration of the pro-survival protein BCL-$X_L$ (22, 24, 29-31). In cells with activated Ras effector pathways, JAK2 inhibition is insufficient to dephosphorylate BAD because of its redundant phosphorylation by the Akt and ERK pathways. These findings suggest that compensatory activation of the Akt and/or ERK pathways may explain the inability of JAK inhibitor monotherapy to reduce the malignant clone burden in JAK2$^{V617F}$ MPN patients, a hypothesis which is supported by both (i) the observation that these Ras effector pathways are hyperactivated in resistant cells (32, 33) and (ii) our finding that co-inhibition of these pathways sensitizes resistant cells to JAK inhibitor therapy. Further, while a diverse array of upstream events may potentially lead to the activation of Ras effector pathways to drive resistance (16), including the overexpression or mutational activation of receptor tyrosine kinases, the stimulation of MPN cells with soluble growth factors or cytokines in their microenvironment, or the mutational activation of either the ERK or AKT effector pathways, our evidence suggests that this is achieved in a subset of JAK2$^{V617F}$ MPN patients through direct activating mutations in KRAS or NRAS.

The results presented here unify several recent findings in the field of JAK2$^{V617F}$ positive MPNs. First, a recent study demonstrated that heterodimerization of JAK2 with JAK1 or TYK2 occurs in JAK2$^{V617}$ cells that are resistant to JAK inhibitors and further hypothesized that this heterodimerization may drive resistance through reactivation of STAT signaling (10). The evidence presented here suggests that resistance in cells with JAK2 heterodimerization may function through the transactivation of Ras effector pathways rather than the reactivation of STAT signaling, as pharmacological inhibition of Ras effector pathways fully resensitizes these cells.

Second, redundant survival signaling through the JAK/STAT, Akt, and ERK pathways described here provides a mechanistic explanation for the limited activities of monotherapies targeting MEK, PI3K/mTOR, and Akt in both drug-sensitive and drug-resistant JAK2$^{V617F}$ cells despite the constitutive activity of these pathways (32, 34, 35)1.

Third, while a previous study identified a correlation between JAK2/STAT/PIM1 activity and BAD phosphorylation in drug-sensitive cells (36), more recent studies have excluded BAD as a potential regulator of apoptosis by demonstrating that phosphorylation levels at Ser$^{136}$ are unchanged by JAK inhibitor treatment. The latter study suggested instead that BIM is the key apoptosis regulator in these cells (37). Our results reconcile these discrepancies by demonstrating that BAD phosphorylation at Ser$^{112}$ is the relevant target of JAK/STAT signaling in drug sensitive cells; that BAD phosphorylation at Ser 112 and 136 by the Ras effectors ERK and Akt, respectively, can rescue JAK inhibitor-induced loss of Ser$^{112}$ phosphorylation; and finally, that BAD phosphorylation is required for survival and Ras effector-mediated drug resistance. BIM, on the other hand, is necessary for the execution of apoptosis via its efficient activation of BAX (38), and its knockdown is sufficient to drive resistance to JAK inhibitors (37), but it acts downstream of BAD.

Fourth, by demonstrating that survival in both sensitive and resistant cells is dependent on BCL-$X_L$, we provide a mechanistic rationale for the recent findings that (i) JAK2$^{V617F}$ cells show marked insensitivity to BCL-2 inhibition (39) and (ii) combination therapy involving a JAK inhibitor combined with a dual BCL-2/BCL-$X_L$ inhibitor (ABT-737) yields improved responses in animal models of JAK2$^{V617F}$ MPN relative to JAK inhibitor monotherapy (32).

Finally, this work suggests that the combined inhibition of JAK2 and Ras effector pathways, or the direct, selective inhibition of BCL-$X_L$, may yield more robust and durable responses in patients than JAK inhibitor monotherapy. In the near term, the former approach may be more tractable, as the direct inhibition of BCL-$X_L$ using early-generation inhibitors has been associated with on-target toxicities (40, 41). Generally, however, our studies suggest that therapies based on the combination of JAK inhibitors with (i) Akt inhibitors; (ii) Akt plus MEK or ERK inhibitors; or (iii) selective BCL-$X_L$ inhibitors, or monotherapies involving selective BCL-$X_L$ inhibitors alone, warrant further investigation.

Materials and Methods.

Cell Lined and Drugs.

All cell lines were grown at 37° C. in 5% $CO_2$. UKE-1 cells were grown in RPMI 1640 with 10% fetal calf serum, 10% horse serum and 1 μM hydrocortisone. HEL92. 1.7 cells were grown in RPMI with 10% fetal bovine serum (FBS) and 1% penicillin/streptomycin. Set2 cells were grown in RPMI with 20% FBS and 1% penicillin/streptomycin. Set2-inhibitor resistant (CYTR and INCBR) and control cells (Parental) were grown as above in media supplemented with 0.7 μM INCB018424, 0.5 μM CYT387, or DMSO respectively. UKE-1 and HEL92.1.7 cells were obtained from Ann Mullally, Brigham and Women's Hospital, and Set2 parental and resistant cell lines were obtained from Ross Levine, Memorial Sloan-Kettering. Drugs were purchased from Selleck Chemicals, ChemieTek, and ApexBio and were used at the following concentrations: 2 μM for VX-11E, 10 μM for MK-2206, 2 μM for AZD-6244, 0.2 μM for BEZ-235 (GI50 assay and western blots), 4 μM for SGI-1776 (western blots and apoptosis assays), 1 μM for INCB and CYT (western blots, BH3 profiling), and 5 μM for INCB, 1.6 μM for ABT-737 and ABT-199, and 0.8 μM for WEHI-539 (apoptosis assays).

Pathway Activating Screen.

We performed pooled lentiviral screens as previously described (14). UKE-1 cells were infected with the pooled library (MOI=0.3) and treated separately with either vehicle (DMSO) or three concentrations of INCB018424 (1 μM, 5 μM, and 10 μM). After three weeks of culture, all drug- and vehicle-treated cells were subjected to genomic DNA purification and PCR-based barcode amplification. Results were de-convoluted as previously described using the Illumina Hi-Seq 2000 sequencing platform.

GI50 Assay.

Cells were seeded into 6-well plates and infected with the desired ORF activating allele or control vector. Lentiviruses were produced and applied as previously described (42). Following two days of puromycin selection (2 µg/ml), infected cells were seeded into 96-well plates at 5,000 cells/well.

To generate GI50 curves, cells were treated with vehicle (DMSO) or an eight-log serial dilution of drug to yield final concentrations of 200, 20, 2, 0.2, 0.02, 0.002, 0.0002, or 0.00002 M. Each treatment condition was represented by at least three replicates. Three to four days after drug addition, cell viability was measured using Cell Titer Glo® (Promega). Relative viability was then calculated by normalizing luminescence values for each treatment condition to control treated wells.

To generate GI50 curves for drug combinations, slight modifications are made. Primary drug was applied and diluted as above while the second drug was kept at a constant concentration across all wells except the DMSO-only condition. Viability for all primary drug dilutions was then calculated relative to luminescence values from the secondary drug-only condition. Dose-response curves were fit using Graph pad/Prism 6 software.

Western Blotting and Antibodies.

Immunoblotting was performed as previously described (42) and membranes were probed with primary antibodies (1:1000 dilution) recognizing p-STAT5, STAT5, p-STAT3, STAT3, BAD, p-BAD Ser112, p-BAD Ser136, p-Akt (Thr308), Akt, p-ERK1/2 (Thr202/Tyr204), ERK1/2, Pim1, BCL-X$_L$, BCL-2, MCL-1, Bim, Bax, Bak, NaATPase, and β-Actin. All antibodies were purchased from Cell Signaling Technology.

shRNA Constructs.

TRC shRNA clones were obtained from Sigma-Aldrich and the Duke RNAi Facility as glycerol stocks. Constructs were prepared in lentiviral form and used to infect target cells as previously described (43).

| Construct | TRC ID | Sequence |
|---|---|---|
| shBAD_54 | TRCN0000033454 | GACGAGTTTGTGGACTCCTTTCTCG AGAAAGGAGTCCACAAACTCGTC (SEQ ID NO: 1) |
| shBAD_56 | TRCN0000033456 | CCAGTCCTGGTGGGATCGGAACTCG AGTTCCGATCCCACCAGGACTGG (SEQ ID NO: 2) |
| shJAK2 (1) | TRCN0000003180 | GCTTTGICTTTCGTGTCATTACTCG AGTAATGACACGAAAGACAAAGC (SEQ ID NO: 3) |
| shJAK2 (2) | TRCN0000003181 | GCAGAATTAGCAAACCTTATACTCG AGTATAAGGTTTGCTAATTCTGC (SEQ ID NO: 4) |

Quantification of Apoptosis by Annexin-V.

Cells were seeded in six-well plates and treated with either the indicated amount of drug or vehicle (DMSO). Cells were incubated for the indicated time, washed twice with ice-cold PBS, and resuspended in IX Annexin V binding buffer (10 mM HEPES, 140 mM NaCl, 2.5 mM CaCl2; BD Biosciences). Surface exposure of phosphatidyl-serine was measured using APC-conjugated Annexin V (BD Biosciences). 7-AAD (BD Biosciences) was used as a viability probe. Experiments were analyzed at 20,000 counts/sample using BD FACSVantage SE. Gatings were defined using untreated/unstained cells as appropriate.

qRT-PCR.

Real-time PCR was performed as previously described (14). Human Pim1; forward primer 5'-TTATCGACCT-CAATCGCGGC-3' (SEQ ID NO:5); reverse primer 5'-GG-TAGCGATGGTAGCGGATC-3' (SEQ ID NO:6); Human GAPDH; forward primer 5'-CCCACTCCTCCACCTTT-GAC-3' (SEQ ID NO:7); reverse primer 5'-ACCCTGTT-GCTGTAGCCAAA-3' (SEQ ID NO:8).

BH3 Profiling.

HMLE, Set2, UKE-1 and HEL92.1.7 cells were BH3 profiled as previously described (38).

Phospho-Null BAD Mutants.

Wild-type and double Ser-to-Ala (S112A/S136A) mutant murine BAD constructs were obtained from Addgene and cloned using the Gateway® system (Life Technologies) into the pLX-303 vector and prepared for lentiviral infection as previously described (44).

Patient Cohort.

The patient cohort consisted of 42 patients. The male to female ratio was 1.8 (27/15). The median age was 75.9 years, ranging from 55.3 to 89.1 years. All patients were diagnosed following the WHO 2008 criteria, including 16 cases with Chronic myelomonocytic leukemia (CMML), 2 with Myelodysplastic/mycloproliferative neoplasm, unclassifiable (MDS/MPN, U), 6 with MPN and 18 with Refractory anemia with ring sideroblasts and thrombocytosis (RARS-T). The study design adhered to the tenets of the Declaration of Helsinki and was approved by our institutional review board before its initiation.

Mutational Analyses.

JAK2V617F mutation was analyzed by melting curve analysis, as described in Schnittger et al. (45) NRAS mutation were analyzed either by melting curve analysis described previously (46) or Next-generation deep-sequencing using the 454 GS FLX amplicon chemistry (Roche Applied Science) as previously described (47). In melting curve analysis positive NRAS cases were subsequently further characterized by Next-generation sequencing. KRAS mutations were either sequenced by the Sanger method or Next-generation deep-sequencing (45, 47).

REFERENCES CITED

1. R. Kralovics, F. Passamonti, A. S. Buser, S. S. Teo, R. Tiedt, J. R. Passweg, A. Tichelli, M. Cazzola, R. C. Skoda, A gain-of-function mutation of JAK2 in myeloproliferative disorders. *The New England journal of medicine* 352, 1779-1790 (2005).
2. R. L. Levine, M. Wadleigh, J. Cools, B. L. Ebert, G. Wernig, B. J. Huntly, T. J. Boggon, I. Wlodarska, J. J. Clark, S. Moore, J. Adelsperger, S. Koo, J. C. Lee, S. Gabriel, T. Mercher, A. D'Andrea, S. Frohling, K. Dohner, P. Marynen, P. Vandenberghe, R. A. Mesa, A. Tefferi, J. D. Griffin, M. J. Eck, W. R. Sellers, M. Meyerson, T. R. Golub, S. J. Lee, D. G. Gilliland, Activating mutation in the tyrosine kinase JAK2 in polycythemia vera, essential thrombocythemia, and myeloid metaplasia with myelofibrosis. *Cancer cell* 7, 387-397 (2005).
3. C. James, V. Ugo, J. P. Le Couedic, J. Staerk, F. Delhommeau, C. Lacout, L. Garcon, H. Raslova, R. Berger, A. Bennaceur-Griscelli, J. L. Villeval, S. N. Constantinescu, N. Casadevall, W. Vainchenker, A unique clonal JAK2 mutation leading to constitutive signalling causes polycythaemia vera. *Nature* 434, 1144-1148 (2005).
4. A. Quintas-Cardama, K. Vaddi, P. Liu, T. Manshouri, J. Li, P. A. Scherle, E. Caulder, X. Wen, Y. Li, P. Waeltz, M. Rupar, T. Burn, Y. Lo, J. Kelley, M. Covington, S. Shepard, J. D. Rodgers, P. Haley, H. Kantarjian, J. S. Fridman, S. Verstovsek, Preclinical characterization of the selective JAK1/2 inhibitor INCB018424: therapeutic implications for the treatment of myeloproliferative neoplasms. *Blood* 115, 3109-3117 (2010).
5. A. Pardanani, T. Lasho, G. Smith, C. J. Burns, E. Fantino, A. Tefferi, CYT387, a selective JAK1/JAK2 inhibitor: in vitro assessment of kinase selectivity and preclinical studies using cell lines and primary cells from polycythemia vera patients. *Leukemia* 23, 1441-1445 (2009).
6. G. Wernig, M. G. Kharas, R. Okabe, S. A. Moore, D. S. Leeman, D. E. Cullen, M. Gozo, E. P. McDowell, R. L. Levine, J. Doukas, C. C. Mak, G. Noronha, M. Martin, Y. D. Ko, B. H. Lee, R. M. Soll, A. Tefferi, J. D. Hood, D. G. Gilliland, Efficacy of TG101348, a selective JAK2 inhibitor, in treatment of a murine model of JAK2V617F-induced polycythemia vera. *Cancer cell* 13, 311-320 (2008).
7. S. Verstovsek, H. Kantarjian, R. A. Mesa, A. D. Pardanani, J. Cortes-Franco, D. A. Thomas, Z. Estrov, J. S. Fridman, E. C. Bradley, S. Erickson-Viitanen, K. Vaddi, R. Levy, A. Tefferi, Safety and efficacy of INCB018424, a JAK1 and JAK2 inhibitor, in myelofibrosis. *The New England journal of medicine* 363, 1117-1127 (2010).
8. A. Pardanani, J. R. Gotlib, C. Jamieson, J. E. Cortes, M. Talpaz, R. M. Stone, M. H. Silverman, D. G. Gilliland, J. Shorr, A. Tefferi, Safety and efficacy of TG101348, a selective JAK2 inhibitor, in myelofibrosis. *Journal of clinical oncology: official journal of the American Society of Clinical Oncology* 29, 789-796 (2011).
9. A. Deshpande, M. M. Reddy, G. O. Schade, A. Ray, T. K. Chowdary, J. D. Griffin, M. Sattler, Kinase domain mutations confer resistance to novel inhibitors targeting JAK2V617F in myeloproliferative neoplasms. *Leukemia* 26, 708-715 (2012).
10. P. Koppikar, N. Bhagwat, O. Kilpivaara, T. Manshouri, M. Adli, T. Hricik, F. Liu, L. M. Saunders, A. Mullally, O. Abdel-Wahab, L. Leung, A. Weinstein, S. Marubayashi, A. Goel, M. Gonen, Z. Estrov, B. L. Ebert, G. Chiosis, S. D. Nimer, B. E. Bernstein, S. Verstovsek, R. L. Levine, Heterodimeric JAK-STAT activation as a mechanism of persistence to JAK2 inhibitor therapy. *Nature* 489, 155-159 (2012).
11. C. R. Chong, P. A. Janne, The quest to overcome resistance to EGFR-targeted therapies in cancer. *Nature medicine* 19, 1389-1400 (2013).
12. M. S. Glickman, C. L. Sawyers, Converting cancer therapies into cures: lessons from infectious diseases. *Cell* 148, 1089-1098 (2012).
13. P. I. Poulikakos, N. Rosen, Mutant BRAF melanomas—dependence and resistance. *Cancer cell* 19, 11-15 (2011).
14. C. A. Martz, K. A. Ottina, K. R. Singleton, J. S. Jasper, S. E. Wardell, A. Peraza-Penton, G. R. Anderson, P. S. Winter, T. Wang, J. C. Rathmell, J. A. Wargo, D. P. McDonnell, D. M. Sabatini, K. C. Wood, Systematic identification of signaling pathways with potential to confer anticancer drug resistance. In revision (*Science*).
15. J. Y. Qin, L. Zhang, K. L. Clift, I. Hulur, A. P. Xiang, B. Z. Ren, B. T. Lahn, Systematic comparison of constitutive promoters and the doxycycline-inducible promoter. *PloS one* 5, e10611 (2010).
16. J. Downward, Targeting RAS signalling pathways in cancer therapy. *Nature reviews. Cancer* 3, 11-22 (2003).
17. J. Deng, N. Carlson, K. Takeyama, P. Dal Cin, M. Shipp, A. Letai, BH3 profiling identifies three distinct classes of apoptotic blocks to predict response to ABT-737 and conventional chemotherapeutic agents. *Cancer cell* 12, 171-185 (2007).
18. M. Certo, V. Del Gaizo Moore, M. Nishino, G. Wei, S. Korsmeyer, S. A. Armstrong, A. Letai, Mitochondria primed by death signals determine cellular addiction to antiapoptotic BCL-2 family members. *Cancer cell* 9, 351-365 (2006).
19. A. G. Letai, Diagnosing and exploiting cancer's addiction to blocks in apoptosis. *Nature reviews. Cancer* 8, 121-132 (2008).
20. T. Ni Chonghaile, K. A. Sarosiek, T. T. Vo, J. A. Ryan, A. Tammareddi, G. Moore Vdel, J. Deng, K. C. Anderson, P. Richardson, Y. T. Tai, C. S. Mitsiades, U. A. Matulonis, R. Drapkin, R. Stone, D. J. Deangelo, D. J. McConkey, S. E. Sallan, L. Silverman, M. S. Hirsch, D. R. Carrasco, A. Letai, Pretreatment mitochondrial priming correlates with clinical response to cytotoxic chemotherapy. *Science* 334, 1129-1133 (2011).
21. J. A. Ryan, J. K. Brunelle, A. Letai, Heightened mitochondrial priming is the basis for apoptotic hypersensitivity of CD4+CD8+ thymocytes. *Proceedings of the National Academy of Sciences of the United States of America* 107, 12895-12900 (2010).
22. S. R. Datta, H. Dudek, X. Tao, S. Masters, H. Fu, Y. Gotoh, M. E. Greenberg, Akt phosphorylation of BAD couples survival signals to the cell-intrinsic death machinery. *Cell* 91, 231-241 (1997).
23. A. Bonni, A. Brunet, A. E. West, S. R. Datta, M. A. Takasu, M. E. Greenberg, Cell survival promoted by the Ras-MAPK signaling pathway by transcription-dependent and -independent mechanisms. *Science* 286, 1358-1362 (1999).
24. J. Zha, H. Harada, E. Yang, J. Jockel, S. J. Korsmeyer, Serine phosphorylation of death agonist BAD in response to survival factor results in binding to 14-3-3 not BCL-X(L). *Cell* 87, 619-628 (1996).
25. X. Fang, S. Yu, A. Eder, M. Mao, R. C. Bast, Jr., D. Boyd, G. B. Mills, Regulation of BAD phosphorylation at serine 112 by the Ras-mitogen-activated protein kinase pathway. *Oncogene* 18, 6635-6640 (1999).
26. T. L. Aho, J. Sandholm, K. J. Peltola, H. P. Mankonen, M. Lilly, P. J. Koskinen, Pim-1 kinase promotes inactivation of the pro-apoptotic Bad protein by phosphorylating it on the Ser112 gatekeeper site. *FEBS letters* 571, 43-49 (2004).
27. R. L. Levine, A. Pardanani, A. Tefferi, D. G. Gilliland, Role of JAK2 in the pathogenesis and therapy of myeloproliferative disorders. *Nature reviews. Cancer* 7, 673-683 (2007).
28. Q. B. She, D. B. Solit, Q. Ye, K. E. O'Reilly, J. Lobo, N. Rosen, The BAD protein integrates survival signaling by EGFR/MAPK and PI3K/Akt kinase pathways in PTEN-deficient tumor cells. *Cancer cell* 8, 287-297 (2005).
29. A. Kelekar, B. S. Chang, J. E. Harlan, S. W. Fesik, C. B. Thompson, Bad is a BH3 domain-containing protein that forms an inactivating dimer with Bcl-XL. *Molecular and cellular biology* 17, 7040-7046 (1997).
30. M. P. Scheid, K. M. Schubert, V. Duronio, Regulation of bad phosphorylation and association with Bcl-x(L) by the MAPK/Erk kinase. *The Journal of biological chemistry* 274, 31108-31113 (1999).
31. E. Yang, J. Zha, J. Jockel, L. H. Boise, C. B. Thompson, S. J. Korsmeyer, Bad, a heterodimeric partner for Bcl-XL and Bcl-2, displaces Bax and promotes cell death. *Cell* 80, 285-291 (1995).
32. M. Waibel, V. S. Solomon, D. A. Knight, R. A. Ralli, S. K. Kim, K. M. Banks, E. Vidacs, C. Virely, K. C. Sia, L. S. Bracken, R. Collins-Underwood, C. Drenberg, L. B.

Ramsey, S. C. Meyer, M. Takiguchi, R. A. Dickins, R. Levine, J. Ghysdael, M. A. Dawson, R. B. Lock, C. G. Mullighan, R. W. Johnstone, Combined targeting of JAK2 and Bcl-2/Bcl-xL to cure mutant JAK2-driven malignancies and overcome acquired resistance to JAK2 inhibitors. *Cell reports* 5, 1047-1059 (2013).
33. W. Fiskus, S. Verstovsek, T. Manshouri, R. Rao, R. Balusu, S. Venkannagari, N. N. Rao, K. Ha, J. E. Smith, S. L. Hembruff, S. Abhyankar, J. McGuirk, K. N. Bhalla, Heat shock protein 90 inhibitor is synergistic with JAK2 inhibitor and overcomes resistance to JAK2-TKI in human myeloproliferative neoplasm cells. *Clinical cancer research: an official journal of the American Association for Cancer Research* 17, 7347-7358 (2011).
34. I. Khan, Z. Huang, Q. Wen, M. J. Stankiewicz, L. Gilles, B. Goldenson, R. Schultz, L. Diebold, S. Gurbuxani, C. M. Finke, T. L. Lasho, P. Koppikar, A. Pardanani, B. Stein, J. K. Altman, R. L. Levine, A. Tefferi, J. D. Crispino, AKT is a therapeutic target in myeloproliferative neoplasms. *Leukemia* 27, 1882-1890 (2013).
35. W. Fiskus, S. Verstovsek, T. Manshouri, J. E. Smith, K. Peth, S. Abhyankar, J. McGuirk, K. N. Bhalla, Dual PI3K/AKT/mTOR inhibitor BEZ235 synergistically enhances the activity of JAK2 inhibitor against cultured and primary human myeloproliferative neoplasm cells. *Molecular cancer therapeutics* 12, 577-588 (2013).
36. J. M. Gozgit, G. Bebernitz, P. Patil, M. Ye, J. Parmentier, J. Wu, N. Su, T. Wang, S. Ioannidis, A. Davies, D. Huszar, M. Zinda, Effects of the JAK2 inhibitor, AZ960, on Pim/BAD/BCL-xL survival signaling in the human JAK2 V617F cell line SET-2. *The Journal of biological chemistry* 283, 32334-32343 (2008).
37. B. Will, T. Siddiqi, M. A. Jorda, T. Shimamura, K. Luptakova, P. B. Staber, D. B. Costa, U. Steidl, D. G. Tenen, S. Kobayashi, Apoptosis induced by JAK2 inhibition is mediated by Bim and enhanced by the BH3 mimetic ABT-737 in JAK2 mutant human erythroid cells. *Blood* 115, 2901-2909 (2010).
38. K. A. Sarosiek, X. Chi, J. A. Bachman, J. J. Sims, J. Montero, L. Patel, A. Flanagan, D. W. Andrews, P. Sorger, A. Letai, BID preferentially activates BAK while BIM preferentially activates BAX, affecting chemotherapy response. *Molecular cell* 51, 751-765 (2013).
39. R. Pan, L. J. Hogdal, J. M. Benito, D. Bucci, L. Han, G. Borthakur, J. Cortes, D. J. Deangelo, L. Debose, H. Mu, H. Dohner, V. I. Gaidzik, 1. Galinsky, L. S. Golfman, T. Haferlach, K. G. Harutyunyan, J. Hu, J. D. Leverson, G. Marcucci, M. Muschen, R. Newman, E. Park, P. P. Ruvolo, V. Ruvolo, J. Ryan, S. Schindela, P. Zweidler-McKay, R. M. Stone, H. Kantarjian, M. Andreeff, M. Konopleva, A. G. Letai, Selective BCL-2 Inhibition by ABT-199 Causes On-Target Cell Death in Acute Myeloid Leukemia. *Cancer discovery* 4, 362-375 (2014).
40. C. Tse, A. R. Shoemaker, J. Adickes, M. G. Anderson, J. Chen, S. Jin, E. F. Johnson, K. C. Marsh, M. J. Mitten, P. Nimmer, L. Roberts, S. K. Tahir, Y. Xiao, X. Yang, H. Zhang, S. Fesik, S. H. Rosenberg, S. W. Elmore, ABT-263: a potent and orally bioavailable Bcl-2 family inhibitor. *Cancer research* 68, 3421-3428 (2008).
41. L. Gandhi, D. R. Camidge, M. Ribeiro de Oliveira, P. Bonomi, D. Gandara, D. Khaira, C. L. Hann, E. M. McKeegan, E. Litvinovich, P. M. Hemken, C. Dive, S. H. Enschede, C. Nolan, Y. L. Chiu, T. Busman, H. Xiong, A. P. Krivoshik, R. Humerickhouse, G. I. Shapiro, C. M. Rudin, Phase I study of Navitoclax (ABT-263), a novel Bcl-2 family inhibitor, in patients with small-cell lung cancer and other solid tumors. *Journal of clinical oncology: official journal of the American Society of Clinical Oncology* 29, 909-916 (2011).
42. K. C. Wood, D. J. Konieczkowski, C. M. Johannessen, J. S. Boehm, P. Tamayo, O. B. Botvinnik, J. P. Mesirov, W. C. Hahn, D. E. Root, L. A. Garraway, D. M. Sabatini, MicroSCALE screening reveals genetic modifiers of therapeutic response in melanoma. *Science signaling* 5, rs4 (2012).
43. D. E. Root, N. Hacohen, W. C. Hahn, E. S. Lander, D. M. Sabatini, Genome-scale loss-of-function screening with a lentiviral RNAi library. *Nature methods* 3, 715-719 (2006).
44. X. Yang, J. S. Boehm, X. Yang, K. Salehi-Ashtiani, T. Hao, Y. Shen, R. Lubonja, S. R. Thomas, O. Alkan, T. Bhimdi, T. M. Green, C. M. Johannessen, S. J. Silver, C. Nguyen, R. R. Murray, H. Hieronymus, D. Balcha, C. Fan, C. Lin, L. Ghamsari, M. Vidal, W. C. Hahn, D. E. Hill, D. E. Root, A public genome-scale lentiviral expression library of human ORFs. *Nature methods* 8, 659-661 (2011).
45. S. Schnittger, U. Bacher, W. Kern, M. Schroder, T. Haferlach, C. Schoch, Report on two novel nucleotide exchanges in the JAK2 pseudokinase domain: D620E and E627E. *Leukemia* 20, 2195-2197 (2006).
46. M. Nakao, J. W. Janssen, T. Seriu, C. R. Bartram, Rapid and reliable detection of N-ras mutations in acute lymphoblastic leukemia by melting curve analysis using LightCycler technology. *Leukemia* 14, 312-315 (2000).
47. A. Kohlmann, G. Martinelli, W. Hofmann, G. Kronnie, S. Chiaretti, C. Preudhomme, E. Tagliafico, J. Hernandez, C. Gabriel, T. Lion, P. Vandenberghe, K. M. Polakova. M. Béné, M. Brueggemann, G. Cazzaniga, A. Yeoh, S. Lehmann, T. Ernst, E. O. Leibundgut, U. Ozbek, K. I. Mills, M. Dugas, C. Thiede, O. Spinelli, L. Foroni, J. H. Jansen, A. Hochhaus, T. Haferlach, The Interlaboratory Robustness of Next-Generation Sequencing (IRON) Study Phase II: Deep-Sequencing Analyses of Hematological Malignancies Performed by an International Network Involving 26 Laboratories. *Blood* 120, Abstract: 1399 (2012).

While this invention has been described in conjunction with the various exemplary embodiments outlined above, various alternatives, modifications, variations, improvements and/or substantial equivalents, whether known or that are or may be presently unforeseen, may become apparent to those having at least ordinary skill in the art. Accordingly, the exemplary embodiments according to this invention, as set forth above, are intended to be illustrative, not limiting. Various changes may be made without departing from the spirit and scope of the invention. Therefore, the invention is intended to embrace all known or later-developed alternatives, modifications, variations, improvements, and/or substantial equivalents of these exemplary embodiments. All technical publications, patents and published patent applications cited herein are hereby incorporated by reference in their entirety for all purposes.

What is claimed is:

1. A method of sensitizing a subject to a JAK2 inhibitor wherein the subject has developed resistance to a JAK2 inhibitor-based therapy and has at least one phosphorylated BAD- and/or activated BCL-XL protein, comprising selecting a subject having developed a myeloproliferative neoplasm resistant to a JAK2 inhibitor-based therapy and has at least one phosphorylated BAD- or activated BCL-XL protein, and administering to the selected subject a therapeutically effective amount of a BCL-XL protein inhibitor in combination with the JAK2 inhibitor, whereby the subject is sensitized to the JAK2 inhibitor.

2. The method of claim 1, wherein the BCL-XL protein inhibitor is administered before or concurrently with the JAK2 inhibitor.

3. The method of claim 1, wherein the BCL-XL protein inhibitor is selected from the group consisting of ABT-737, ABT-263, ABT-199, Genasense, obatoclax, and combinations thereof.

4. The method of claim 2, wherein the BCL-XL protein inhibitor is selected from the group consisting of ABT-737, ABT-263, ABT-199, Genasense, obatoclax, and combinations thereof.

5. The method of claim 1, wherein the method further comprises obtaining a biological sample from the subject, and detecting within the sample at least one phosphorylated BAD- or activated BCL-XL protein, wherein the presence of phosphorylated BAD protein or activated BCL-XL protein indicated JAK2-inhibitor-based therapy resistance.

6. The method of claim 5, wherein the biological sample is a cancer biopsy.

7. The method of claim 1, wherein the myeloproliferative neoplasm is selected from the group consisting of chronic myeloid leukemia, acute myeloid leukemia, polycythaemia vera, essential thrombocythemia, primary myelofibrosis, chronic eosinophilic leukemia, chronic myelomonocytic leukemia, systemic mastocytosis, idiopathic myelofibrosis, and myeloma.

8. The method of claim 1, wherein the JAK-2 inhibitor is selected from the group consisting of INCB018424/Ruxolitinib, Tofacitinub, Baricittnib, CYT387, Lestaurtinib, Pacritinib, TG101348, and combinations thereof.

9. The method of claim 8, wherein the JAK-2 inhibitor is INCB018424.

10. The method of claim 1, wherein the BCL-XL protein inhibitor and the JAK2 inhibitor are administered co-currently.

11. The method of claim 1, wherein administration of the BCL-XL protein inhibitor and JAK-2 inhibitor reduces or inhibits cancer cell growth within the subject.

* * * * *